(12) United States Patent
Brugidou et al.

(10) Patent No.: US 7,132,514 B1
(45) Date of Patent: Nov. 7, 2006

(54) MEANS FOR IDENTIFYING A NOVEL CLASS OF GENES RESISTANT TO THE RICE YELLOW MOTTLE VIRUS AND THE LOCUS OF A MAJOR GENE OF RESISTANCE TO THE VIRUS, AND THEIR APPLICATIONS

(75) Inventors: Christophe Brugidou, Pignan (FR); Jean-Paul Brizard, Saint Martin de Londres (FR); Alain Ghesquiere, Montpellier (FR)

(73) Assignee: IRD, Paris Cedex (FR)

( * ) Notice: Subject to any disclaimer, the term of this patent is extended or adjusted under 35 U.S.C. 154(b) by 607 days.

(21) Appl. No.: 10/018,433

(22) PCT Filed: Jun. 21, 2000

(86) PCT No.: PCT/FR00/01723

§ 371 (c)(1),
(2), (4) Date: Feb. 11, 2002

(87) PCT Pub. No.: WO00/79001

PCT Pub. Date: Dec. 28, 2000

(30) Foreign Application Priority Data

Jun. 21, 1999 (FR) .................................. 99 07831

(51) Int. Cl.
*C07K 1/14* (2006.01)
*C07K 1/26* (2006.01)

(52) U.S. Cl. ..................................... 530/412
(58) Field of Classification Search ................ 530/412
See application file for complete search history.

(56) References Cited

U.S. PATENT DOCUMENTS 4,235,869 A * 11/1980 Schwarzberg ............... 436/512
5,898,097 A    4/1999 Gafny et al.

FOREIGN PATENT DOCUMENTS

EP         0244207 A1 * 11/1987
WO       WO 98 30721      7/1998

OTHER PUBLICATIONS

Opalka et al. "Movement of rice yellow mottle virus between xylem cells through pit membranes" Proc. Natl. Acad. Sci. Mar. 1998 vol. 95 pp. 3323-3328.*
Citovsky, V. "Probing Plasmodesmal Transport with Plant Viruses" Plant Physiol. 1993 vol. 102, pp. 1071-1076.*
Citovsky, V. Tobacco mosaic virus: a pioneer of cell-to-cell movement. Philosophical transactions of the Royal Society of London. Series B, Biological sciences. Mar. 29, 1999, 354 (1383) p. 637-43.*
Dorokhov et al. A novel function for a ubiquitous plant enzyme pectin methylesterase: the host-cell receptor for the tobacco mosaic virus movement protein. FEBS letters, Nov. 19, 1999, 461 (3) p. 223-8.*
Jackson, D. Opening up the communication channels: Recent insights into plasmodesmal function. Current Opinion in Plant Biology 3 (5): p. 394-399 Oct. 2000.*
Bonneau et al, "Expression of the rice yellow mottle virus P1 protein in vitro and in vivo and its Involvement in virus spread", VIROLOGY, vol. 244, No. 1, Apr. 25, 1998, pp. 79-86.
Opalka et al, "Movement of rice yellow mottle virus between xylem cells through pit membranes", Proceedings of the National Academy of Sciences of the United States, vol. 95, No. 6, Mar. 17, 1998, pp. 3323-3328.
Albar et al, "Genetic basis and mapping of the resistance to rice yellow mottle virus: I. QTLs identification and relationship between resistance and plant morphology", Theoretical and Applied Genetics, (Nov. 1998) vol. 97, No. 7, pp. 1145-1154.
Pressoir et al, "Genetic basis and mapping of the resistance to rice yellow mottle virus: II. Evidence of a complementary epistasis between two QTLs", Theoretical and Applied Genetics, (Nov. 1998) vol. 97, No. 7, pp. 1155-1161.
DATABASE: Wing et al, "A BAC sequencing framework to sequence the rice genome", Jun. 10, 2000, DATABASE entry/Accession No. AZ132900.

* cited by examiner

*Primary Examiner*—Mary E. Mosher
(74) *Attorney, Agent, or Firm*—Nixon & Vanderhye P.C.

(57) ABSTRACT

The invention concerns a method for capturing the target proteins indispensable to the infectious cycles of a pathogenic virus, in particular the rice yellow mottle virus (RYMV) and for cloning the genes involved in said processes. The invention therefore concerns a method for identifying molecular markers of the resistance to RYMV. The method involves the isolation of said protein complexes with viral particles. The method consists in subjecting the samples containing said complexes to electrophoresis and Western Blot using a capsid anti-protein monoclonal antibody, and in recuperating the non-immunodetected bands. The invention also concerns a cDNA capable of being hybridized with a BAC (Bacterial Artificial Chromosome) screened from a bank consisting of DNA fragments of a variety of rice such as IR64. Said BAC clone contains DNA sequences of the markers identified from the rice by means of a process which consists in comparing the AFLP (Amplified Length Polymorphism) of resistant and sensitive rice plants.

5 Claims, 15 Drawing Sheets

(a) : 183 F2 IR64 x Gigante (b) : 328 F2 IR64 x Gigante

Figure 12

A — Injection buffer only pH8.5 — 14040004.bio - 100.0 μl

B — Injection 170 m RYMV pH8.5 — 20040002.bio - 100.0 μl — Method 1

Figure 12 cont.

Injection 170 mg RYMV pH8.5
after dialysis O/N 4°C 11050003.bio - 100.0 µl

C

260 nm / 280 nm vs Min 11050004.bio - 100.0 µl

Injection 170 mg RYMV pH8.5

Method 2

D

260 nm / 280 nm vs Min

MW f.B14 f.B13 f.B12 f.B11 f.B10 f.B9 f.B4 f.B3 f.B2 f.B2 f.B3 f.B4 f.B9 f.B10 f.B11 f.B12 f.B13 f.B14 MW

MW f.B23 f.B22 f.B21 f.B20 f.B19 f.B18 f.B17 f.B16 f.B15 f.B15 f.B16 f.B17 f.B18 f.B19 f.B20 f.B21 f.B22 f.B23 MW

Gel 13

MW f.B33 f.A30 f.A29 f.A28 f.A18 f.A17 f.A16 f.A3 f.A2 f.A2 f.A3 f.A16 f.A17 f.A18 f.A28 f.A29 f.A30 f.B33 MW

MEANS FOR IDENTIFYING A NOVEL CLASS OF GENES RESISTANT TO THE RICE YELLOW MOTTLE VIRUS AND THE LOCUS OF A MAJOR GENE OF RESISTANCE TO THE VIRUS, AND THEIR APPLICATIONS

This application is the US national phase of international application PCT/FR00/01723 filed Jun. 21, 2000 which designated the U.S.

The invention relates to the means, tools and methods for identifying a new class of resistance genes to the Rice Yellow Mottle Virus (RYMV) and the locus of a major resistance gene to the virus.

In respect of tools, it particularly concerns proteins that are essential to the infectious cycle as well as markers and PCR primers, and their applications to the physical mapping of gene resistance and to gene cloning.

RYMV is a virus that is endemic in Africa. It has common characteristics with the other sobemoviruses; namely only one single-stranded RNA having positive polarity that is non-polyadenylated and of small size, and icosahedric particles of T=3 symmetry produced in very large quantities in the plant. The viral particles also occur in great number in the vascular tissues, mainly the vessels. In a few rare varieties of the African species of cultivated rice *Oryza glaberrima*, a very high resistance to RYMV has been identified. But since the interspecific hybrids between the two species of cultivated rice are extremely sterile, prior research has not been able to describe either the genetic bases or the mechanism of this resistance.

Research by the inventors in this area has shown that a variety called Gigante which originated from Mozambique and was identified by ADRAO, and which is a member of the cultivated Asian rice species *Oryza sativa*, shows the same characteristics as those observed with *O. glaberrima*. The inventors have characterized RYMV resistance by demonstrating that it is related to a major recessive resistance gene that is identical in both sources of resistance under consideration (*O. Sativa* and *O. glaberrima*).

This resistance occurs at the level of cell-to-cell movement and leads to blockage of the virus at the infected cells whereas virus replication is normal.

The work by the inventors on RYMV has shown that this virus moves and multiplies differently throughout the infectious cycle. In inoculated leaves (I, FIG. 11), it is in the form of a complex of viral RNA and viral proteins (capsid proteins, P1 and possibly P3) that it moves locally by crossing through the plasmodesmata of the epidermis cells, mesophyll cells, perivascular sheath cells (mestoma and sheath cell) to reach the vascular cells (phloem and xylem parenchyma) (II, FIG. 11). In the vascular cells, before the so-called long-distance movement, it encapsulates itself and stabilizes in the form of a compact particle in the vacuole with an acid pH by means of the $Ca_2^+$ divalent ions (II, FIG. 11). Systemic infection can only take place if a large number of stable particles are produced. In systematically infected leaves, the virus leaves the conductor tissues to multiply either in the young vascular tissues, or in the mesophyll cells. At this stage of the infection, local movement occurs in de-capsulated form (complex of viral RNA and proteins) or encapsulated but always through the plasmodesmata (III, FIG. 11).

During these different steps of the infectious cycle, the viral complex and/or the virion need to be identified and conveyed by proteins of the plant in order to move from one cell compartment to another, from one cell to another.

For example, the plant proteins connected with the transport of the virus or its complex appear to have a similar function (transport) but are specific to the tissue being crossed (epidermis, mesophyll, mestoma, perivascular sheath, phloem, xylem). When these proteins are translated from the wild allele, it is the susceptibility proteins which enable the virus to move. The muted allele, on the other hand, seems to lead either to a less functional protein (partial resistance) or to a non-functional protein (total resistance).

It is therefore considered that these proteins belong to a family of genes whose common cell function is apparently recognition of the substrate and transport through the plasmodesmata, but these proteins are different as regards tissue specificity (epidermis, mesophyll, mestoma, perivascular sheath, phloem, xylem).

Regulation of symplastic transport is most probably the essential function of this family of genes.

RYMV is also a very stable virus and occurs in the cells in several isoforms of which three have been determined: compact, swollen and intermediate. Therefore, depending upon cell pH (cytoplasm 7–8, vacuoles, vesicles and vessels 4,5–6.5) the conformation and outer charge of the particle vary. This charge enables it to attach to the membranes and to enter a healthy cell via an endocytosis mechanism. Finally, at cell level, the inventors have shown that this virus accumulates chiefly in the vacuoles. The in planta presence of three isoforms, the compartmenting and viral accumulation in partially resistant plants have therefore made it possible to put forward an original mechanism for RYMV tolerance, as distinct from resistance.

RYMV tolerance appears to take place by means of accumulation in the vacuoles. The tonoplast, by physically separating the viral particles from the cell compartment, apparently prevents any harmful interaction for cell machinery. Therefore, the virus multiplies, accumulates without killing the cell (therefore no symptoms).

The association between the host cell and the virus is such that the plant behaves like a storage plant.

In this model, the co-evolution between virus and host plant led the virus to adapting itself and being finally recognized by the plant as a simple reserve protein produced by the plant, conveyed via the reticulum and Golgi apparatus towards the vacuole. Intense invagination of the tonoplast (autophagy mechanism) might enable the virus produced in the cytoplasm to accumulate in the vacuole.

In addition, this mechanism is also similar to the one observed in cell detoxification for heavy metals or salt for example.

Having regard to these results, the inventors first prepared a method for identifying proteins involved in the recognition and targeted transport of pathogenic viruses in plants, and for cloning the genes involved in these processes.

The purpose of the invention is therefore to provide a method for capturing the target proteins that are indispensable to the infectious cycle of a pathogenic virus, especially the RYMV virus, and concerns the proteins so isolated.

A further purpose of the invention is to provide a method for identifying molecular markers of the resistance locus to RYMV.

It also concerns the DNA fragments, as such, as revealed by this method and which can be used as markers.

The invention also concerns applications of such markers, in particular to define other markers having high specificity to the resistance locus and to predict a resistant phenotype.

The invention particularly concerns the application of said markers to determine a physical map of resistance and for gene cloning.

The invention further relates to sequences of primers, as new products, used in the PCR techniques applied.

The method for isolating proteins involved in the recognition and targeted transport of a pathogenic virus circulating via the plasmodesmata in a plant is characterized in that samples containing complexes of said proteins with viral particles are subjected to electrophoresis and Western blot using a capsid anti-protein monoclonal antibody, and the non-immunodetected bands are then collected.

According to one variant, the complex is obtained from a virus extracted from infected sensitive plants.

The virus is more particularly the RYMV virus and proteins of 5, 24, 42, 49, 59, 66, 70, 77 and 210 kDa are collected.

According to another variant, the complex is obtained from a purified virus and contacted with the proteins of a cell suspension of a sensitive plant.

In particular, the virus is the RYMV virus and proteins of 24, 45, 51, 57, 63, 85 and beyond 120 kDa are collected.

The proteins such as obtained by the above-defined method also come within the scope of the invention as new products.

The invention concerns the application of these proteins, in particular for the cloning of resistance genes to pathogenic viruses circulating via the plasmodesmata in a plant.

The invention also concerns the identification of markers of the locus of a major resistance gene to RYMV, comprises the use of AFLP markers (Amplified Fragments Length Polymorphism) and uses the PCR technique.

This method of identification is characterized in that it comprises:

selective amplification of rice DNA fragments firstly from resistant individuals and secondly from sensitive individuals, descending from parent varieties, these fragments being previously submitted to a digestion step, followed by ligation to fix complementary primer adapters having, at their end, one or more specific nucleotides, one of the primers in the primer pair being labelled for development purposes, separating the amplification products by gel electrophoresis under denaturing conditions, and comparing the electrophoresis profiles obtained with mixtures of fragments derived from resistant descendants and with mixtures derived from sensitive descendants, with the fragments derived from parent varieties, for the purpose of identifying bands whose polymorphism is genetically linked to the resistance locus, this identification being optionally followed, for validation purposes, by verification on each of the individuals and by calculation of the genetic recombination rate between the marker and the resistance locus.

In one embodiment of the invention, the DNA fragments are obtained by digestion of the genomic DNAs of resistant plants and of sensitive plants, and their parents, using restriction enzymes.

Restriction enzymes which have proved to be suitable include EcoRI and MseI.

Short nucleotide sequences are fixed to digestion fragments (adapters) to generate blunt ends to which the adapters are subsequently fixed.

The primers used in the amplification step are complementary to these adapters with, at their 3' end, from 1 to 3 nucleotides which may be variable.

The amplification step is advantageously conducted using the PCR technique.

Specific amplification profiles are obtained with primer pairs respectively having AAC and CAG, ACC and CAG motifs at their end, or further AGC and CAG.

The sequences corresponding to the EcoRI and MseI adapters are respectively GAC TGC GTA CCA ATT C (SEQ ID NO 1) and GAT GAG TCC TGA GTA A (SEQ NO 2).

The primer pairs used for amplification are then advantageously chosen from among E-AAC/M-CAG; E-ACC/M-CAG; and E-AGC/M-CAG; in which E and M respectively correspond to SEQ ID NO 1 and SEQ ID NO 2. Other pairs are given in table 6 in the examples.

Comparative study of the amplification profiles obtained reveals polymorphic bands specifically present in the sensitive varieties and their sensitive descendants, as shown in the examples, and consequently corresponding to resistance markers.

In particular, development by gel electrophoresis under denaturing conditions leads to identifying 2 marker bands M1 and M2 of respectively 510 bp and 140 bp.

According to analysis of segregation data, these 2 bands determine a chromosome segment of 10 to 15 cM carrying the resistance locus and are located either side of this locus at 5–10 cM.

According to one provision of the method of the invention, the polymorphic bands identified as markers specific to the RYMV resistance locus, are isolated from gels. Advantageously the electrophoresis gels are excised. This isolation step is followed by purification using conventional techniques. In this manner DNA fragments are obtained.

According to another provision of the invention, said purified fragments are cloned in an appropriate vector, such as a plasmid, inserted into the host cells, in particular bacterial cells such as those of E. coli.

According to another provision of the invention, the purified, cloned DNA fragments are sequenced.

Taking advantage of the sequences of the inserts corresponding to said DNA fragments, the invention also provides a method for obtaining markers having high specificity for the locus of a major resistance gene to RYMV. This method is characterized in that PCR primer pairs are determined which are complementary to the fragments of the sequence of a given insert, specific amplification of the insert is made using these primer pairs, and the amplification products are then subjected to migration on electrophoresis gel.

These DNA sequences can be used to identify a polymorphism linked to the resistance locus in a rice variety to be examined using different methods as described in the examples:

1) by directly identifying a size polymorphism of these DNA sequences after specific amplification and separation of the fragments on agarose gel, 2) by digesting the amplification products with restriction enzymes to separate the digestion products on agarose gel, 3) by using these sequences as probes to hybridize the DNA of rice varieties previously digested by a restriction enzyme and to determine a restriction polymorphism.

The invention concerns, as new products, the polymorphous AFLP bands such as identified by the method defined above, from the DNA of rice plants, optionally isolated, purified and sequenced.

These AFLP bands are characterized in that they are specifically revealed in a variety sensitive to RYMV (IR64) and in the fraction of sensitive plants derived from the crossing of this variety with the Gigante resistance variety as described in the examples.

The invention particularly concerns the DNA sequences corresponding to these polymorphous bands, which can be used to define a segment of chromosome 4 of 10–15 cM carrying the resistance locus to RYMV.

Having regard to the method with which they are obtained, the AFLP bands correspond to restriction fragments and in particular, according to one embodiment of the method of the invention, to EcoRI-MseI fragments.

Fragments of this type are called M1 and M2 markers and are characterized by a size, of 510 bp and 140 bp respectively, in electrophoresis gel under denaturing conditions.

These fragments are characterized in that they correspond to DNA sequences flanking the resistance locus and located either side of the latter at 5–10 cM.

The invention concerns a cDNA such as defined above, characterized in that said DNA sequences corresponding to said polymorphous bands, carry the resistance locus to RYMV and define a segment smaller than 10 cM.

The invention also concerns fragments cloned in vectors such as plasmids, these cloning vectors as such, characterized in that they comprise such fragments, and the host cells transformed using these vectors, such as bacterial cells, for example E. coli. The invention relates in particular to the DNA sequence corresponding to the fragment identified as M1 marker and meeting the following sequence SEQ ID NO 3:

CGTGCTTGCTTATAGCACTACAGGAGA
AGGAAGGGGAACACAACAGCCATGGCGAGCGAA
GGTTCAACGTCGGAGAAACAGGCTGCGACGGGCA
GCAAGGTGCCGGCGGCGGATCGGAG-
GAAGGAAAAGGAGGAAATCGA AG
TTATGCTGGAGGGGCTTGACCTAAGGGCAGATGA
GGAGGAGGATG TGGAATTGGAGGAAGATCTAGAG-
GAGCTTGAGGCAGATGCAAGATGG CTAGCCCTAG-
CAACAGTTCATACGAAGCGATCGTT-
TAGTCAAGGGGCT TTCTTTGGGAGT
ATGCGCTCAGCATGGAACTGCGCGAAAGAAGTA
GAT TTCAGAGCAATGAAAGACAATCTGT-
TCTCGATCCAATTCAATTGTTTG GGGGATTGG-
GAACGAGTTATGAATGAAGGTCCAT
GGACCTTTCGAGGATGTTC
GGTGCTCCTCGCAGAATATGATGGCTGGTCCAAG
ATTGAAT

The DNA sequence of the M1 marker has a size of 471 bp.

The invention also concerns, as new products, the sequences of nucleotides used as PCR amplification primers.

Such primers comprise the pairs E-AAC/M-CAG; E-ACC/M-CAG; E-ACC/M-CAG; in which E and M respectively relate to SEQ ID NO 1 and SEQ ID NO 2.

Other primers are complementary to sequences identified in the sequence of the fragment designated by marker M1. These are in particular (5',3') sequences chosen from among:

```
AGGAAGGGGAACACAACAGCC  (21 bp)  (SEQ ID N°4)

TTATGCTGGAGGGGCTTGACC  (21 bp)  (SEQ ID N°5)

GCAGTTCCATGCTGAGCGCAT  (21 bp)  (SEQ ID N°6)

CCGAACATCCTCGAAAGGTCC  (21 bp)  (SEQ ID N°6)

TCATATTCTGCGAGGAGCACC  (21 bp)  (SEQ ID N°8)
```

The invention also concerns the DNA sequence corresponding to the fragment identified as marker M2 and corresponding to sequence SEQ ID NO 9

```
AATTCACCCCATGCCCTAAG TTAGGACGTT CTCAGCTTAG

TGGTGTGGTA GCTTTTTCTA TTTTCCTAAG CACCCATTGA

AGTATTTTGC ATTGGAGGTG GCCTTAGGTTTGCCTCTGTTA
```

The size of M2 is 120 bp.

Specific primers complementary to sequences identified in the sequence of M2 were defined. Said sequences meet the following sequencing (5',3'):

SEQ ID NO 10

AACCTAAGGCCACCTCCAAT

SEQ ID NO 11

GCAAACCTAAGGCCACCTC

SEQ ID NO 12

ATTCACCCCATGCCCTAAG

According to a further aspect of the invention, the latter concerns the use of DNA sequences obtained with the above primers to define polymorphisms which can be used to identify resistant phenotypes.

The invention also concerns a method for identifying the DNA sequence carrying the major resistance gene to RYMV. This method is characterized by screening a bank consisting of DNA fragments of 100 to 150 kb of the IR64 or other variety, such as the BAC bank (Bacterial Artificial Chromosomes) cloned in bacteria, to select the clone or clones from the bank containing the markers defined above and the resistance gene to RYMV.

This type of BAC bank is available from the IRRI institute.

To identify the gene of the selected clone or clones, the raw protein juice extracted from plants is used to identify the fraction and then step by step the protein which, when placed in the presence of the purified virus, enables cell-to-cell movement within the resistant variety. The candidate protein or proteins are then partially sequenced either from the N-terminal end, or from internal fragments released by hydrolysis. In this manner, primers can be defined and used to amplify the corresponding cDNA. For validation purposes, it is verified that these cDNA will necessarily go and hybridise the BAC clones positioned in the space between the microsatellite markers.

As a variant, it is possible to sub-clone the BAC fragment containing the gene into elements of smaller size in the form of cosmids which are subsequently re-arranged so as to cover the entire initial BAC clone. The cosmids are used in genetic engineering to perform a functional complementation test used to validate the sequence contained in the cosmid and corresponding to the cDNA isolated using the protein approach. In this case the purpose is to demonstrate that synthesis of the protein responsible for cell-to-cell virus movement makes it possible to render the resistant variety sensitive.

The invention therefore concerns a cDNA able to hybridize with a BAC clone screened from a bank as described above containing DNA fragments of 100 to 150 kb of a rice variety such as IR64, for example from a BAC bank (Bacterial Artificial Chromosomes), this BAC clone belonging to a contig (or group of overlapping BAC clones) of BAC clones containing the DNA sequences of the markers identified from rice using the method defined above.

In accordance with the invention, the resistance gene may be transferred to sensitive varieties in conventional manner using specific genetic markers bound to it. In this way resistant varieties may be developed in much faster, easier manner.

It is a further point of interest that the sequence of this gene facilitates access to the resistance genes of other viruses (Potyvirus for example) which are pathogenic for other plants, but characterized by the same mechanism (cell-to-cell movement). The invention therefore provides means of great interest for plant improvement based on natural resistances to plant pathogens.

Other characteristics and advantages of the invention will be given in the following examples, in which reference is made to FIGS. 1 to 15.

BRIEF DESCRIPTION OF THE FIGURES

FIG. 12: the chromatographs of viruses extracted from infected sensitive plants.

EXAMPLES

Example 1

Identification of Resistant-Source Varieties

Figure 1:
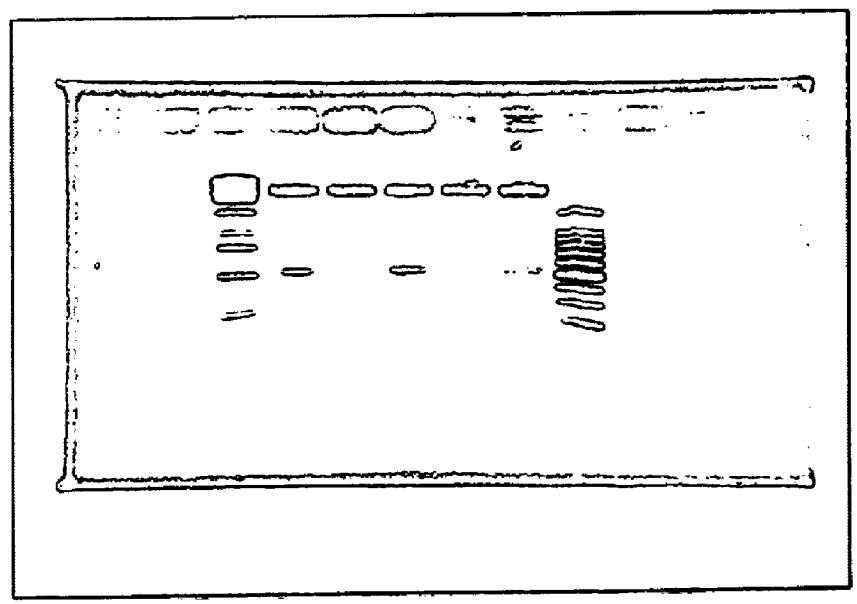
FIG. 1: cloning of marker M1 in the PGEMTeasy plasmid. Digestion of the plasmid shows a DNA fragment of 510 bp corresponding to band M1.

The varieties used in the resistance study, and especially the two resistant varieties Gigante and Tog5681, were characterized using microsatellite markers on a representative sampling of loci.

Polymorphism is evidenced by the number of repeats of a short nucleotide pattern, most often binucleotide which is characteristic of a given variety.

On a set of loci, the catalogued alleles can provide specific characteristics for each variety.

The detection of these microsatellite markers is made by DNA amplification using the specific primers determined by Chen et al (1) followed by migration on polyacrylamide gel under denaturing conditions in accordance with the protocol described by the same authors.

Table 1 gives the results using a reference system drawn up by Chen et al above, according to which the alleles are identified by the number of pattern repeats compared with the IR36 variety used as control. The two varieties Gigante and Tog5681 are therefore specifically described on 15 loci in respect of any other varieties (the microsatellite markers are given in column one).

TABLE 1

| Locus | Chr | Size on IR36 | Ref. | IR36 | Gigante | IR64 | Azucena | Tog568113 |
|-------|-----|--------------|------|------|---------|------|---------|-----------|
| RM001 | 1   | 113          | (2)  | n    | n − 26  | n    | n − 22  | n − 26    |
| RM005 | 1   | 113          | (2)  | n    | n − 6   | n − 4| n + 16  | n − 8     |
| RM011 | 7   | 140          | (2)  | n    | n − 4   | n    | n − 24  | n − 16    |
| RM018 | 7   | 157          | (2)  | n    | n + 4   | n + 6| n + 8   | n − 6     |
| RM019 | 12  | 226          | (2)  | n    | n       | n + 21| n − 9  | n − 21    |
| RM021 | 11  | 157          | (2)  | n    | n + 8   | n    | n − 14  | n − 32    |
| RM148 | 3   | 129          | (3)  | n    | n + 6   | n    | n       | n + 6     |

TABLE 1-continued

| Locus | Chr | Size on IR36 | Ref. | IR36 | Gigante | IR64 | Azucena | Tog568113 |
|---|---|---|---|---|---|---|---|---|
| RM167 | 11 | 128 | (3) | n | n + 4 | n | n + 32 | n + 24 |
| RM168 | 3 | 116 | (3) | n | n − 20 | n | n − 20 | n − 24 |
| RM232 | 3 | 158 | (1) | n | n − 14 | n | n − 12 | n − 16 |
| RM022 | 3 | 194 | (2) | n | n − 2 | n | n − 4 | n − 2 |
| RM252 | 4 | 216 | (1) | n | n + 38 | n + 2 | n − 20 | n + 10 |
| RM255 | 4 | 144 | (1) | n | n | n | n | n |
| RM246 | 1 | 116 | (1) | n | n − 12 | n − 12 | n − 16 | n − 12 |
| RM231 | 3 | 182 | (1) | n | n + 6 | n − 22 | n − 4 | n − 12 |

Example 2

Characterization of Resistance

Resistance was characterized using artificial inoculation of young seedlings with the virus, compared with an extremely sensitive control variety IR64.

The virus content was followed up for 60 days after inoculation using ELISA tests on the most recent leaves.

These tests were never able to demonstrate a signal that was significantly different to the signal of control plants non-inoculated with the virus.

A further experiment was conducted by inoculating isolated protoplasts of the two varieties Tog5681 and Gigante. In both cases, it was possible to detect the presence of viral proteins (capsid protein and P1 movement protein) and the accumulation of viral DNA, demonstrating the capacity of these protoplasts to multiply the virus, in the same manner as the protoplasts of sensitive varieties such as IR64.

Therefore, if it is considered that replication, cell-to-cell movement and long-distance transport through the vessels are the three main steps in the process of the infectious cycle within the plant, the resistance of these two varieties most logically lies in blockage of the virus at the infected cells.

Example 3

Resistance Genetics

Different F1 crosses were made between the resistant *O. sativa* variety (Gigante), a resistant *O. glaberrima* variety (Tog5681—also identified by ADRAO), and the highly sensitive control variety IR64 (selected at the IRRI).

Culture of the plant material, crosses and production of descendants were made in the IRD greenhouses in Montpellier.

The F1 hybrids obtained between the sensitive and resistant varieties were tested for resistance to the RYMV virus by ELISA testing and follow-up of symptoms.

These F1 hybrids proved to be as sensitive as the sensitive parent, and therefore showed that that the type of resistance is recessive.

On the other hand, the hybrids between the two resistance sources Gigante and Tog5681 only yielded resistant F1 hybrids to the benefit of a single resistance locus in these sources of resistance.

These results are summarized in Table 2 below.

This table gives the distribution of ELISA responses (A 405 nm) in the leaves infected by systemic route of F1 hybrids, of backcrosses and of F2 descendants obtained from backcrosses between the sensitive IR64 variety and the 2 resistant cultivars Gigante and Tog5681.

TABLE 2

| F1 hybrid descendants | Presence of symptoms | Number of genotypes | Distribution of OD values | | | Average values OD |
|---|---|---|---|---|---|---|
| | | | (0.01–0.05) | (0.9–1) | >1 | |
| Derivatives of Tog5681 | | | | | | |
| F1: (IR64 × Tog 5681) | Sensitive | — | — | — | 10 | 1.9 |
| BCS: (IR64 × Tog 5681) × IR64 | Sensitive | 19 | 6 | 4 | 15 | 1.6 |
| BCS: (IR64 × Tog5681 c Tog5681 | In segregation | 22 | 12 | — | 10 | — |
| Derivatives of fertile BCS plant | | | | | | |
| BCS F2 | Sensitive | 11 | — | — | 11 | 1.3 |
| BCS × IR64 | Sensitive | 1 | — | — | 1 | 1.9 |
| BCS × Tog5681 | sensitive | 15 | — | — | 15 | 1.9 |
| Gigante derivatives | | — | — | — | | |
| F1 (IR64 × Gigante) | | — | — | — | 10 | 1.9 |
| F2: (IR64 × Gigante) | In segregation | 65 | 15 | — | 50 | — |
| F1: (Gigante × Tog5681) | Sensitive | — | 10 | — | — | 0.3 |

The ELISA responses were obtained from:
i) 10 plants regenerated by cuttings for each F1 hybrid combination
ii) 1 plant regenerated for each backcross-derived interspecific genotype
iii) direct tests on young seedlings (inoculation at 10 days after germination and read-off at 7 days after inoculation) for F2 and fertile interspecific descendants In respect of Gigante, the heredity of resistance was confirmed by a resistance test on 55 F3 families resulting from the cross between (IR64×Gigante) The results are given in Table 3.

This table gives the segregation of RYMV resistance in F3 descendants (IR64×Gigante). Inoculation was made 10 to 17 days after germination with the Burkina Faso isolate and symptoms were followed up for 45 days after inoculation.

TABLE 3

| Classes of resistance | Number of descendants | Number of plants | | | Incidence of resistant plants |
|---|---|---|---|---|---|
| | | Total | Sensitive | Resistant | |
| Sensitive | 15 | 191 | 191 | 0 | 0 |
| In segregation | 30 | 343 | 262 | 01 | 0.24 |
| | | | | | 2 = 0.07 (3:1) |
| Resistant | 4 | 45 | 14 | 31 | 0.69 |
| Very resistant | 6 | 87 | 0 | 87 | 1 |
| Resistant* | 7 | 73 | 23 | 50 | 0.60 |
| Very resistant* | 4 | 56 | 0 | 56 | 1 |

*F3 descendants derived from resistant F2 plants analysed by ELISA tests

Examination of this table shows that:

¼ of F2 plants only give resistant plants in F3 descendants, and are homozygote for resistance, ¼ of F2 plants only give sensitive plants in F3 descendants, and are homozygote for sensitivity, ½ of F2 plants are in segregation for resistance and give sensitive and resistant plants in the same proportion (3:1) in F3 descendants.

All these results tally perfectly with a single recessive resistance gene occurring in the two varieties Gigante and Tog5681.

Example 4

Identification M1 and M2 Resistance Markers Using the AFLP Protocol a—Obtaining DNA Pools The leaves of 10 sensitive plants and 10 resistant plants derived from an F2 (IR64×Gigante) were sampled for their DNA extraction.

The DNA were then mixed stoechiometric fashion to form two DNA pools respectively corresponding to 10 sensitive or resistant F2 plants and with a final mixture concentration of 50 ng/µl. These mixtures served as basis for the identification of resistance markers using the AFLP (Amplified Fragments Length Polymorphism) method developed by Zaneau et al (4) and Vos et al (5). The products used are in the form of a commercial kit (Gibco BRL) available from Keygene & Life Technologies.

b—Obtaining Restriction Fragments 250 ng of each of the DNA pools at 50 ng/µl and of the parents are digested simultaneously by two restriction enzymes (EcoRI and MseI).

Digestion Reaction (25 µl):
  5 µl DNA (50 ng/ml)
  0.2 µl (2 U) EcoRI (10 U/µl)
  0.2 µl (2 U) MseI (5 U/µl)
  5 µl 5×T4 ligase buffer
  14.5 µl $H_2O$ The digestion reaction is carried out for two hours at 37° C., then for 15 min at 70° C. to inactivate the restriction enzymes. After digestion, the ligation reaction was performed.

Ligation Reaction (50 µl):
  25 µl double digestion reaction medium
  1 µl EcoRI adapter
  1 µl MseI adapter
  5 µl 5×T4 ligase buffer
  1 µl (1 U) ligase (10 U/l)
  17 µl $H_2O$ The ligation reaction is conducted at 37° C. for 3 hours followed by inactivation of the enzyme at 60° C. for 10 min.

c—Amplification

Amplification properly so-called was performed in two steps: preamplification and specific amplification.

c1—Preamplification Reaction (50 µl)
  5 µl of reaction medium containing the digested DNA fixed to the adapters, diluted to 1/10
  0.5 µl EcoRI primer (150 ng/µl)
  2 µl 5 mM nucleotide mixture
  5 µl 10× buffer, Promega
  5 µl $MgCl_2$, 25 mM
  0.2 µl (1 U) Taq polymerase (5 U/µl)
  31.8 µl $H_2O$ The characteristics of PCR pre-amplification are the following:

| 20 cycles with | denaturing: | 30 sec at 94° C. |
|---|---|---|
| | hybridization: | 30 sec at 56° C. |
| | elongation: | 1 min at 72° C. |

Selective amplification is made using an aliquot of the first amplification diluted to 1/30 using primers having 3 selective nucleotides at the 3' end, and by labelling one of the primers to develop bands on autoradiography film.

The following primer pairs are used:
  E-AAC/M-CAG
  E-ACC/M-CAG
  E-AGC/M-CAG in which E meets the sequence:

GAC TGC GTA CCA ATT C (SEQ ID NO 1), and

M meets the sequence:

GAT GAG TCC TGA GTA A (SEQ ID NO 2)

The hybridization temperature is reduced by 0.7° C. per cycle, throughout the 11 following cycles:

| last 20 cycles: | denaturing: | 30 sec at 90° C. |
|---|---|---|
| | hybridization: | 30 sec at 56° C. |
| | elongation: | 1 min at 72° C. |

The EcoRI primer is labelled (for 0.5 μl tube):
0.18 μl EcoRI primer (5 ng)
0.1 μl γ$^{33}$P ATP (10 mCu/μl)
0.05 μl 10×kinase buffer
0.02 μl (0.2 U) T4 polymerase kinase (10 U/μl)
0.15 μl H$_2$O The labelling reaction is conducted at 37° C. for 1 hour and is halted by 10 minutes at 70° C.

c2—Specific Amplification Reaction
(20 μl):
0.5 μl labelled EcoRI primer
5 μl preamplification reaction medium, diluted to 1/30
0.3 μl MseI primer (100 ng/μl)
0.8 μl 5 mM nucleotide mixture
2 μl 10× buffer, Promega
2 μl MgCl$_2$, 25 mM
0.1 μl (0.5 U) Taq polymerase (5 U/μl)
9.3 μl H$_2$Oa Amplification characteristics are as follows:
32 cycles with

| for the first cycle: | | |
|---|---|---|
| denaturing: | 30 sec at 94° C. | |
| hybridization: | 30 sec at 65° C. | |
| elongation: | 1 min at 72° C. | | for the 11 following cycles: the same conditions as previously, reducing the hybridization temperature by 0.7° C. for each cycle; and

| for the 20 last cycles: | | |
|---|---|---|
| denaturing: | 30 sec at 90° C. | |
| hybridization: | 30 sec at 56° C. | |
| elongation: | 1 min at 72° C. | | d) Electrophoresis and Autoradiography

At the end of the amplification reaction, 20 μl of charge buffer are added (98% formamide, 0.005% xylene cyanol and 0.005% bromophenol blue). The amplification products are separated by electrophoresis on denaturing polyacrylamide gel (6% acrylamide, 8 M urea) with a TBE migration buffer (18 mM Tris, 0.4 mM EDTA, 18 mM boric acid, pH 8.0) for 3 hours' migration at a power of 50 watts. After migration, the gel is fixed in a solution of 1 part acetic acid/2 parts absolute ethanol for 20 minutes. The gel is transferred to 3M Wattman paper and dried for 45 minutes at 80° C. with a gel drier. The gel is placed in a cassette with ultrasensitive film. The autoradiograph is developed after two days' exposure. Comparison of the profiles obtained with the parents and the pools of sensitive of resistant plants led to identifying bands present in one of the pools but absent in the other. These bands, candidates for resistance marking, were then verified individually on each of the plants forming the DNA pools.

e) Results

Study of the results obtained shows that the two markers called M1 and M2 are present in the sensitive parent (IR64) and in all F2 plants (IR64×Gigante) forming the pool of sensitive plants, whereas this band is absent in the resistant parent (Gigante) and that only one individual in the resistant pool shows this band. The same type of variation is observed in backcross (IR64×Tog55681)×Tog 5681. The other markers identified by this analysis (M3 to M6) also show the same variation:

presence of bands in the sensitive parent and the pool of F2 sensitive plants (IR64×Gigante) and in the sensitive plants of the backcross (IR64×Tog5681)×Tog5681).

absence of bands in the resistant parents Gigante and Tog5681, in the pool of F2 resistant plants (IR64×Gigante) and in the resistant plants of the backcross (IR64×Tog5681)×Tog5681.

The segregation data between the AFLP markers M1 to M6, the resistance locus for the F2 pools (IR64×Gigante) and the interspecific backcross (IR64×Tog5681)×Tog5681 are summarized in tables 4 and 5. Analysis of the segregation data and of the rare recombinants observed in both crosses can be used to assess the recombination rates between these different markers and the resistance locus. In particular, markers M1 firstly and markers M2 to M6 secondly determine a segment of less than 10–15 cM carrying the resistance locus. M1 and M2 are therefore less than 5–10 cM apart and are positioned either side of this locus.

TABLE 4

| Resistance | N° of individuals observed | | | | | | |
|---|---|---|---|---|---|---|---|
| Phenotype | Resistant | | | Sensitive | | | |
| Marker M1 | | | | | | | |
| RYMV resistance genotype | tt/gg | tt | gg | lt | lt | lt | lt |
| AFLP marker | −/− | +/− | +/ | −/− | +/− | −/− | +/ |
| Resistant F2 pool (IR64 × Gigante) | 10 | — | 1 | — | — | — | — |
| Sensitive F2 pool (IR64 × Gigante) | — | — | — | — | — | 0 | 10 |
| Interspecific backcross Tog5681 | 11 | 1 | — | 0 | 8 | — | — |
| Marker M2, M3, M4, M6 | | | | | | | |
| RYMV resistance genotype | tt/gg | tt | gg | lt | lt | ll | ll |
| AFLP marker | −/− | +/− | +/ | −/− | +/− | −/− | +/ |
| Resistant F2 pool (IR64 × Gigante) | 11 | — | 0 | — | — | — | — |
| Sensitive F2 pool (IR64 × Gigante) | — | — | — | — | — | 0 | 10 |
| Interspecific backcross Tog5681 | 10 | 2 | — | 0 | 8 | — | — |
| Marker M5 | | | | | | | |
| RYMV resistance genotype | tt/gg | tt | gg | lt | lt | ll | ll |
| AFLP marker | −/ | +/− | +/ | −/− | +/− | −/− | +/ |
| Resistant F2 pool (IR64 × Gigante) | 11 | — | — | — | — | — | 0 |
| Sensitive F2 pool (IR64 × Gigante) | — | — | — | — | — | 0 | 10 |
| Interspecific backcross Tog5681 | 9 | 3 | 0 | 8 | — | — | — |

TABLE 5

| Marker M1/Markers M2, M3, M4, M6 | N° individuals observed | | | |
|---|---|---|---|---|
| Genotype M1 | −/* | +/* | −/− | −/− |
| Genotype M2, M3, M4, M6 | +/* | −/− | +/* | −/− |
| Resistant F2 pool (IR64 × Gigante) | 0 | 1 | 0 | 10 |
| Sensitive F2 pool (IR64 × Gigante) | 10 | 0 | 0 | 0 |
| Interspecific backcross Tog5681 | 11 | 2 | 2 | 11 |
| Marker M1/Marker M5 | N° individuals observed | | | |
| Genotype M1 | −/* | +/* | −/− | −/− |
| Genotype M5 | +/* | −/− | +/* | −/− |
| Resistant F2 pool (IR64 × Gigante) | 0 | 1 | 0 | 10 |
| Sensitive F2 pool (IR64 × Gigante) | 10 | 0 | 0 | 0 |
| Interspecific backcross Tog5581 | 11 | 2 | 3 | 10 |
| Marker M5/Markers M2, M3, M4, M6 | N° individuals observed | | | |
| Genotype M5 | +/* | +/* | −/− | −/− |
| Genotype M2, M3, M4, M6 | +/* | −/− | +/* | −/− |
| Resistant F2 pool (IR64 × Gigante) | 0 | 0 | 0 | 11 |
| Sensitive F2 pool (IR64 × Gigante) | 10 | 0 | 0 | 0 |
| Interspecific backcross Tog5681 | 13 | 1 | 0 | 12 |

*(−) interspecific backcross Tog5681 (+ or −) F2 pool.

Example 5

Isolation of Marker M1

A further amplification with the same pair of primers was conducted, followed by migration on polyacrylamide gel under the same conditions as above. Development was carried out by staining with silver nitrate using the silver staining kit (Promega) for direct viewing of the bands on the gel. After development, the M1 band was excised from the gel, then the DNA was eluted in 50 μl water at 4° C. overnight.

An aliquot of 5 μl was taken and re-amplified using the same primer pairs with $P^{33}$ labelling. The amplification product was again separated on 6% denaturing acrylamide gel and compared with the parents and the sensitive and resistant pools. The lane corresponding to this amplification product shows a single band of 510 bp migrating at exactly the same level as the original band which had been excised. Another 5 μl aliquot was also amplified with the same primers and separated on 1.8% agarose gel. The band corresponding to the expected size (510 bp) was again excised and purified with a gene clean kit (Promega).

Example 6

Cloning and Sequencing of the M1 Marker—Cloning

3 μl of purification product was used for a cloning reaction overnight at 37° C.

3 μl purification product
1 μl PGEMTeasy vector
1 μl 10×T4 ligase buffer
1 μl T4 DNA Ligase
4 μl H₂O Transformation was conducted with the E. Coli strain JM109, adding 5 μl of cloning product to 100 μl competent E. Coli JM109 cells. A pre-culture was made on LB culture medium for 1 hour at 37° C. The bacteria were subsequently spread over a Petri dish containing agar with 1/1000 ampicilline. 50 μl IPTG-XGal were added just before spreading the bacteria to select the transformed bacteria. A white colony (transformed) was selected and replaced in culture under the same conditions (Agar plus ampicilline).

From this culture a miniprep of plasmid DNA was MADE using the Wizard Plus kit (Promega). The plasmid DNA containing the insert was digested with the EcoRI enzyme to verify the presence of the M1 marker. 1.8% agarose gel was used to verify the presence of the 3 kb band corresponding to the plasmid and the 510 bp band corresponding to the M1 marker (photo 1).

Sequencing

The sequence of the insert (SEQ ID NO 3) is the following (5',3'):

```
SED ID N°3
         20        30        40        50        60        70
GTGCTTGCTTATAGCACTACAGGAGAAGGAAGGGGAACACAACAGCC

ATGGCGAGCGAAGGTTCAACGTCGGAGAAACAGGCTGCGACGGGCAG

CAAGGTGCCGGCGGCGGATCGGAGGAAGGAAAAGGAGGAAATCGAA

GTTATGCTGGAGGGGCTTGACCTAAGGGCAGATGAGGAGGAGGATGT

GGAATTGGAGGAAGATCTAGAGGAGCTTGAGGCAGATGCAAGATGGC

TAGCCCTAGCCACAGTTCATACGAAGCGATCGTTTAGTCAAGGGGCTT

TCTTTGGGAGTATGCGCTCAGCATGGAACTGCGCGAAAGAAGTAGATT

TCAGAGCAATGAAAGACAATCTGTTCTCGATCCAATTCAATTGTTTGG

GGGATTGGAACGAGTTATGAATGAAGGTCCATGGACCTTTCGAGGAT

GTTCGGTGCTCCTCGCAGAATATGATGGCTGGTCCAAGATTGAAT
```

The sequences corresponding to the primers used for AFLP amplifications were found and show that the band corresponds to a restriction fragment (EcoRI-MseI).

By deducing the sequences corresponding to the primers, the actual size of the DNA fragment of the cloned rice is 471 bp.

Figure 2:
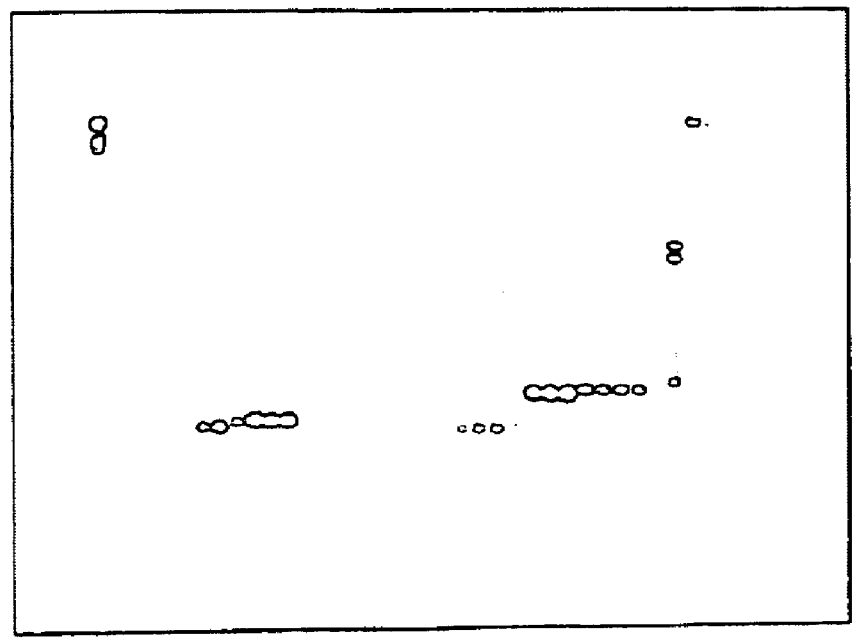
FIG. 2: amplification of marker M1 in the four rice varieties (Azucena, Gigante, IR64 and Tog5681) using the primer pairs (2-4): 291 bp; (2-5): 310 bp; (1-3): 288 bp; (1-4): 406 bp; (1-5): 425 bp; (2-3). The M1 fragment is slightly bigger in Tog5681 than in the other varieties.

The use of different pairs of primers (1-3), (1-4), (1-5) firstly and (2-3), (2-4), (2-5) secondly, makes it possible to validate the cloning of the AFLP M1 band. Amplification of the DNA of the varieties used in the crosses with these primers only shows one single band. The fragment corresponding to the Tog5681 variety is slightly larger than for the other varieties (FIG. 2).

Example 7

Transformation of the M1 Sequence Into a Polymorphous Marker

Figure 3:
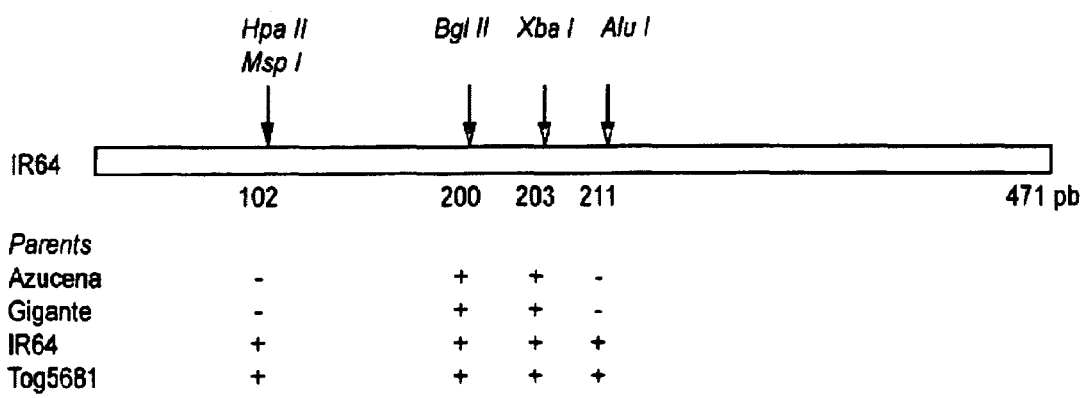
FIG. 3: identification of restriction sites on the sequence of the M1 marker in the 4 varieties IR64, Azucena, Gigante and Tog5681.
Figure 4:
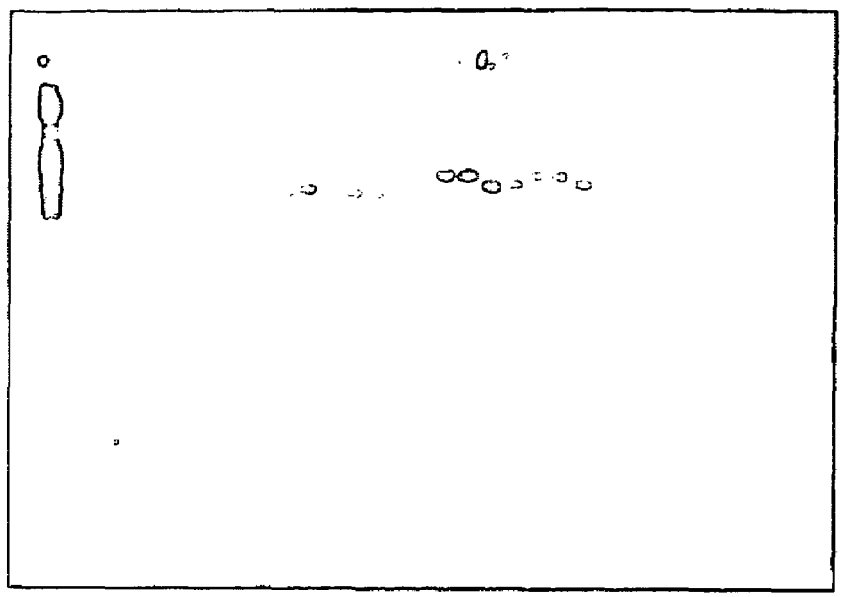
FIG. 4: digestion of the M1 marker with the HpaII enzyme after PCR amplification using primer pairs (1-3), (1-4) and (1-5) on the four varieties (Azucena, Gigante, IR64 and Tog5681). The presence of a HpaII restriction site in the IR64 and Tog568 varieties releases a fragment of 86 bp which reduces the size of the amplified fragment to the same extent.

A polymorphism for the M1 marker was determined between the parents of the doubled haploid population (IR64×Azucena). This population totals over 300 markers distributed over the 12 rice chromosomes. On this account, we relied on the restriction sites of the M1 marker sequence determined on the IR64 parent (FIG. 3). The primers (1-3), (1-4) and (1-5) were used to amplify the DNA of the parents of crossed plants which was then digested by restriction enzymes. The restriction site HpaII/MspI releases a fragment of 86 bp when primer 1 is used. This site is absent in the Gigante and Azucena varieties (FIG. 4).

Figure 5:
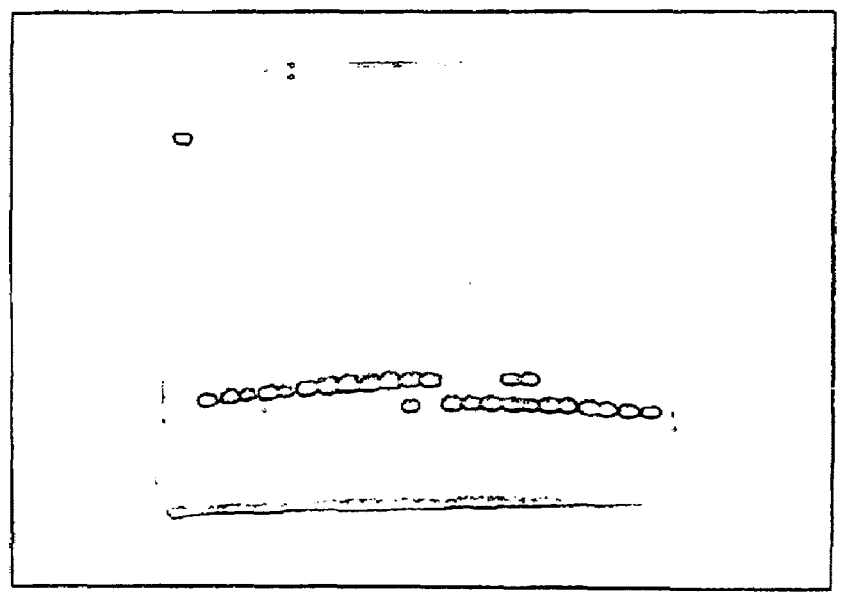
FIG. 5: characterization of the M1 marker on sensitive and resistant plants of F2 issue (IR64 and Gigante). The resistant F2 plants have the profile of the resistant parent (IR64— no HpaII site), with the exception of a single recombinant, the resistant plants have the profile of the sensitive parent (IR64-presence of HpaII site) with the exception of two recombinants.

The marker was tested on the F2 individuals of the sensitive pool and resistant crossed pool (IR64×Gigante). All the resistant individuals have the profile of the Gigante variety (absence of the M1 AFLP marker associated with absence of the restriction site HpaII/MspI) with the exception of individual (5.11). The sensitive individuals show the HpaII/MspI restriction site in the homozygote state like the IR64 variety with the exception of two heterozygote individuals which are recombinant (FIG. 5).

The sequence of the M1 marker which can be amplified with specific primers indeed corresponds to the M1 AFLP marker. Digestion by the HpaII/MspI enzyme leads to distinguishing between the allele derived from the sensitive parent (IR64) and from the resistant parent (Gigante).

With these new data, it is possible to give back-up to the positioning of the resistance locus between markers M1 and M2 and to estimate the recombination rate at 0.065±0.045 for the distance between M1 and the resistance locus, and 0.11±0.047 for the distance between markers M1 and M2.

Example 8

Mapping of the M1 Marker

Figure 6:
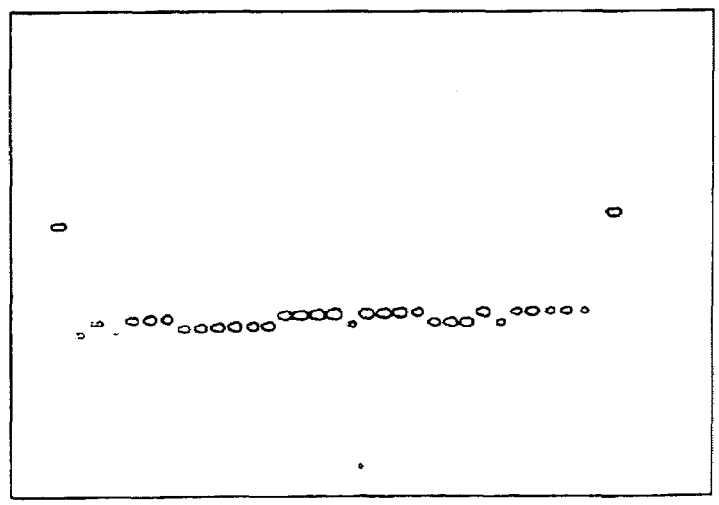
FIG. 6: segregation of the M1 marker in the HD population (IR64×Azucena); IR64-Azucena-30 HD individuals (IR64×Azucena)
Figure 7:
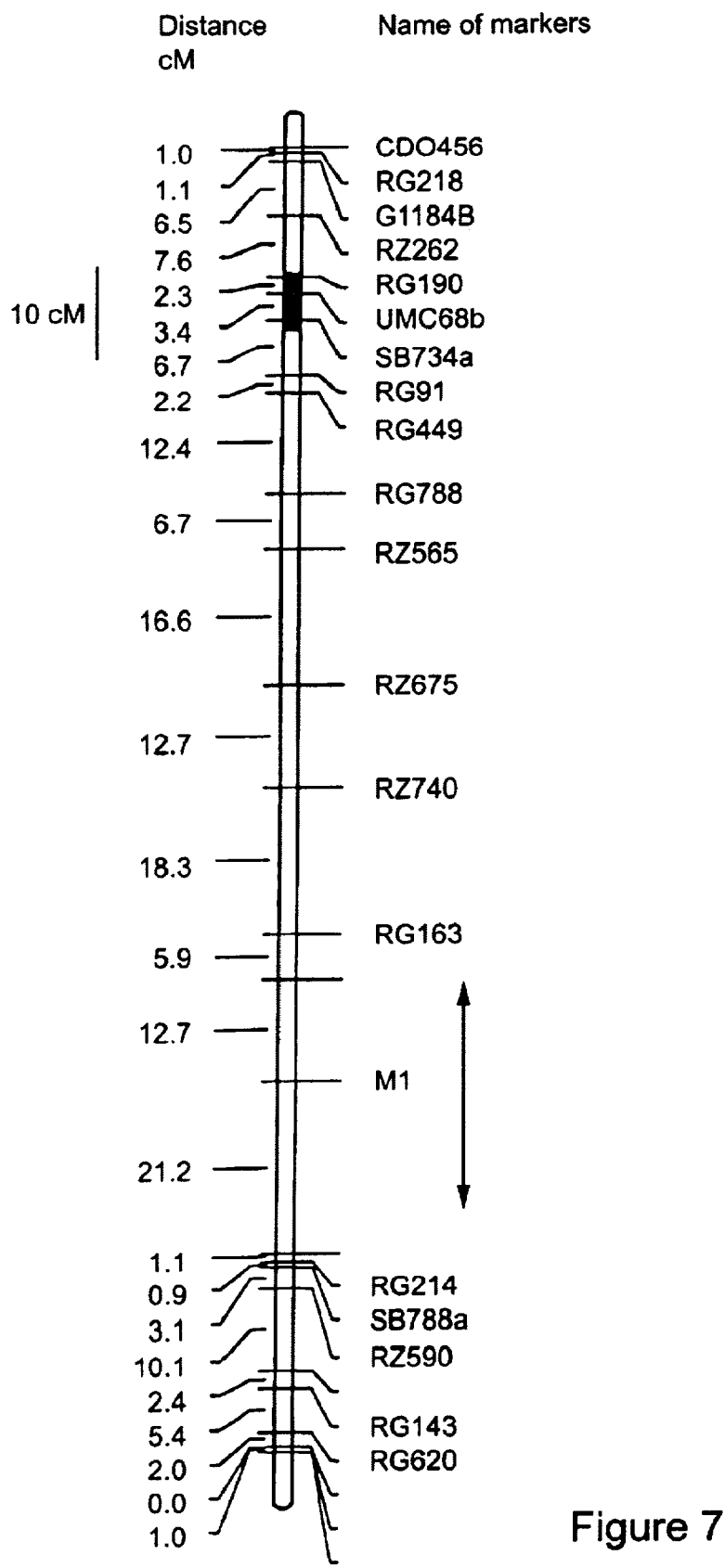
FIG. 7: the genetic linkage map of chromosome 4 of rice with the positioning of marker M1 and identification of the space interval in which the resistance locus is found.
Figure 8:
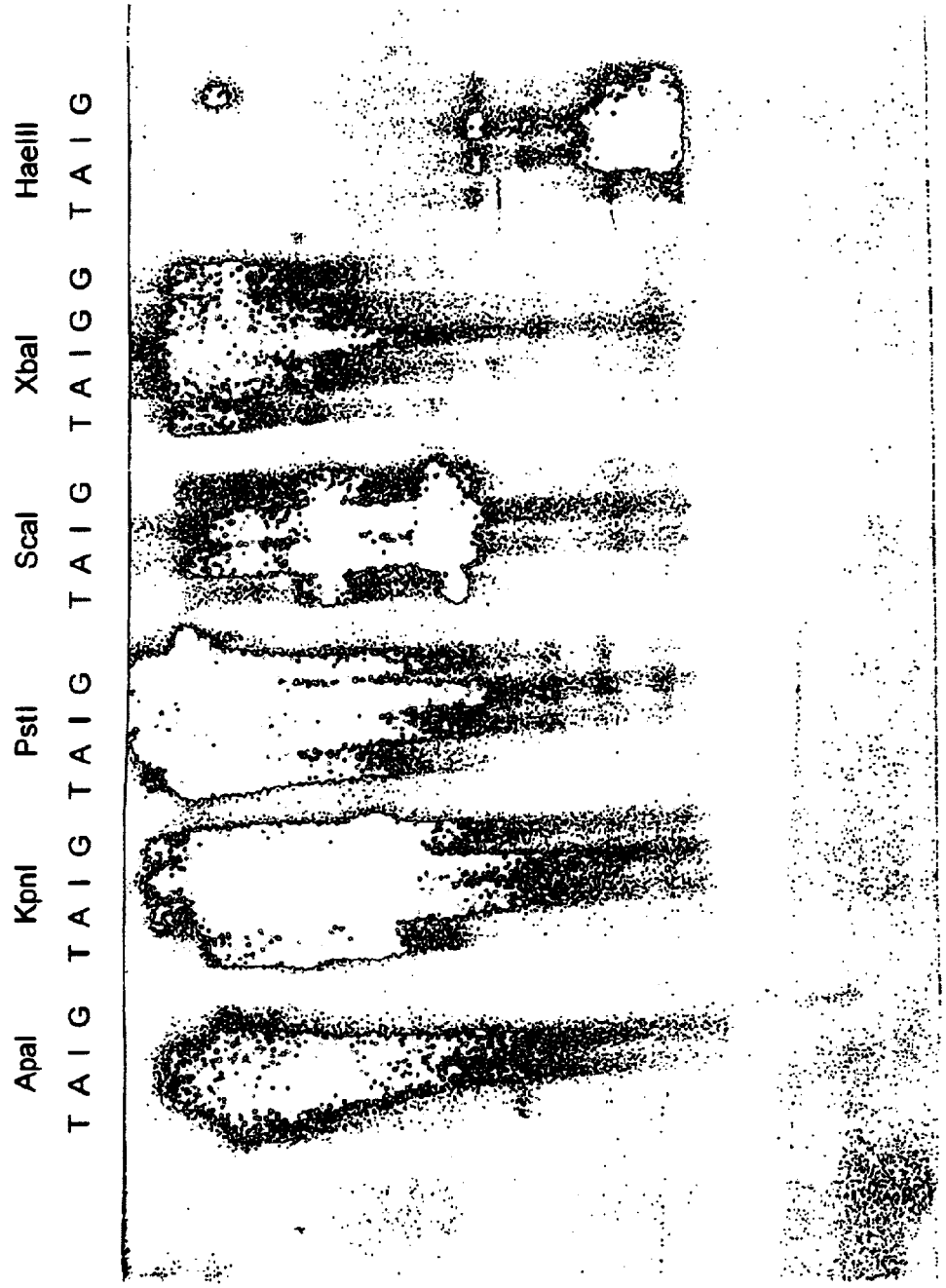
FIG. 8: hybridization of M1 marker used as probe on membranes carrying the DNA of the 4 varieties (IR64, Azucena, Gigante and Tog5681) digested by 6 restriction enzymes ApaI, KpnI, PstI, ScaI, HaeIII. The Tog5681 variety shows a different restriction profile to the other varieties for the ScaI enzyme which may be used to label the resistance locus of this variety.
Figure 9:
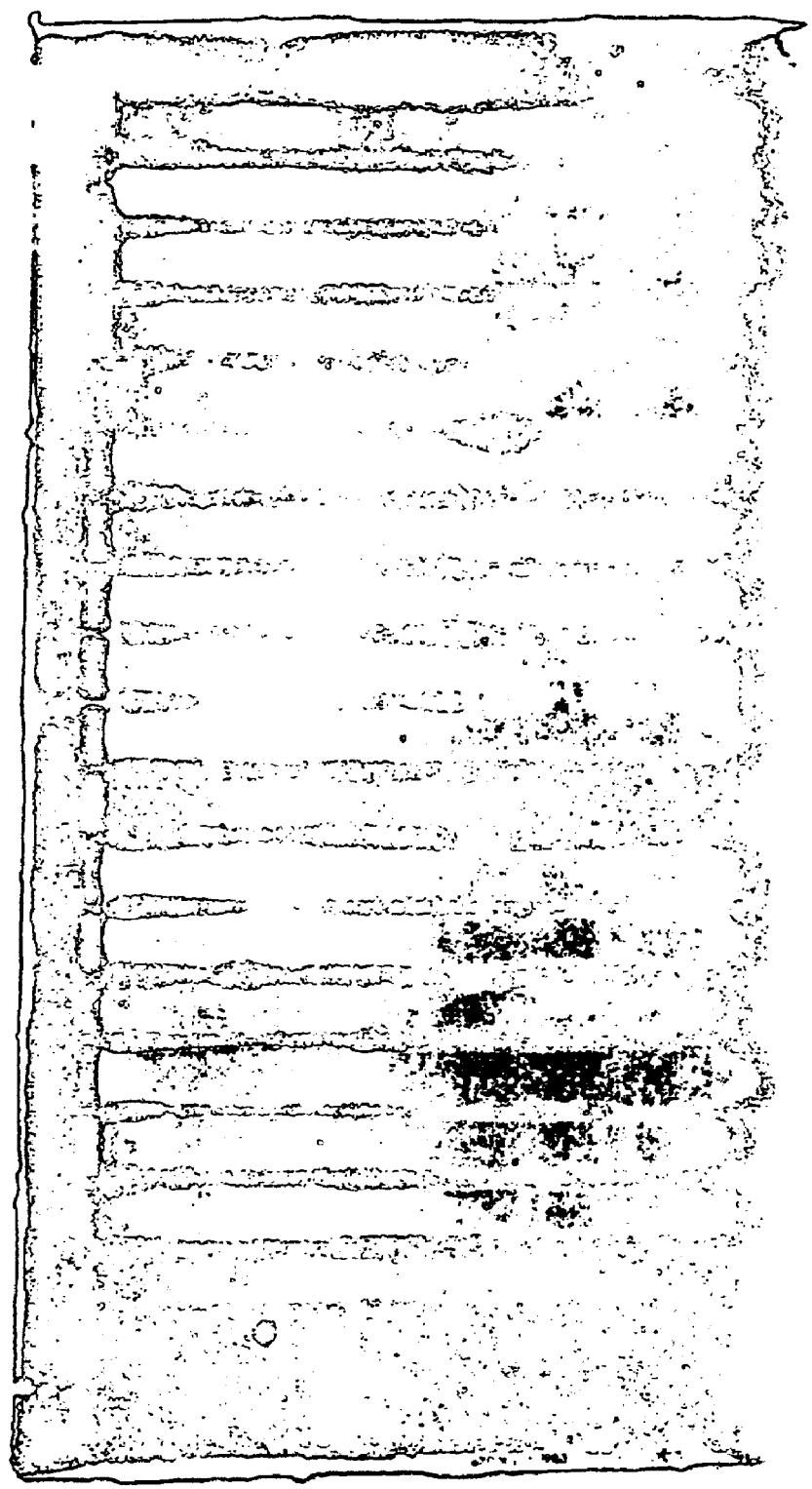
FIG. 9: hybridisation of the M1 marker used as probe on membranes carrying the DNA of individuals derived from backcross (IR64×Tog568)×Tog 5681 and digested with the ScaI enzyme. These descendants are in segregation for RYMV resistance. The sensitive individuals (5) all show the IR64 band associated with the Tog5681 band (heterozygote individuals). The resistant individuals (9) only show the Tog5681 band with the exception of one recombinant individual.

Sixty individuals from the (IR64×Azucena) population were passed as marker M1: amplification with primers (1-3) and digestion with the HpaII/MspI enzyme, followed by separation of the fragments on 2.5% agarose gel. Segregation of marker M1 shows no distortion (FIG. 6). The results are used to map the M1 marker using mapping software (Mapmaker V3) which leads to positioning the M1 marker on chromosome 4 between the markers RG 163 and RG 214 (FIG. 7). This space represents the zone in which the RYMV resistance locus is located.

Mapping of the RYMV resistance gene on chromosome 4 of the genetic map for rice makes it possible to identify the markers the nearest to the resistance locus. They are in particular the microsatellite markers RM252 and RM273, or any other marker within the (4–5 cM) space defined by these markers which can be used to identify polymorphism between the parents IR64 and Gigante, such as the RFLP markers derived from genomic banks or cDNA, microsatellites, AFLP markers or markers derived from physical mapping of the region such as the clones BAC, YAC or their cosmids.

The markers identified in accordance with the invention, or any other marker positioned within this space, with which it is possible to identify a polymorphism between resistant varieties such as Gigante or *O. glaberrima* with RYMV sensitive rice varieties, may be used for transfer of RYMV resistance to sensitive varieties by successive backcrosses followed by marker-assisted selection.

Example 9

Marking the Resistance Locus of the Tog5681 Variety

The presence of the restriction site HpaII/MspI in the Tog5681 variety means that it is not possible to use the strategy in example 8 to verify that the M1 marker is also a marker of Tog5681 resistance derived from Tog5681. Therefore, the 4 varieties Azucena, Gigante, IR64 and Tog5681 were digested with 12 restriction enzymes (BamHI, Bg/II, DraI, EcoRI, EcoRV, HindIII, ApaI, KpnI, PstI, ScaI, XbaI, HaeIII) to identify a restriction polymorphism using the DNA sequence of the M1 marker as probe. The ScaI enzyme leads to identifying a polymorphism between IR64 and Tog5681 (FIG. 8). This polymorphism was used to validate the M1 marker on a backcross (IR64×Tog5681)×IR64 in segregation for resistance. 5 sensitive individuals of this backcross were tested and all showed the characteristic band of IR64. The 9 resistant individuals only show the Tog5681 band with the exception of only one which is recombinant (FIG. 9). The restriction polymorphism revealed by the ScaI enzyme using the M1 marker as probe is therefore related to the resistance locus of Tog5681. There is coherence between genetic analysis and the identification of resistance markers for considering that the M1 marker indeed maps the same resistance locus in the two varieties Gigante and Tog5681.

Example 10

Cloning and Sequencing of the M2 Marker into a Specific PCR-Marker

The AFLP band obtained with the pair of primers E-ACC/M-CAG corresponding to the M2 band visible in the sensitive parent (IR64) and present in all the individuals forming the sensitive pool, was cloned using the same protocol as for marker M1. The sequence corresponding to this band was determined and 3 primers were defined (1 forward—2 reverse) to allow conversion of this marker into a specific PCR marker. Sequence of the M2 marker (120 bp) (SEQ ID NO 9):

```
AATTCACCCC ATGCCCTAAG TTAGGACGTT CTCAGCTTAG
TGGTGTGGTA GCTTTTTCTA TTTTCCTAAG CACCCATTGA
AGTATTTTGC ATTGGAGGTG GCCTTAGGTT TGCCTCTGTTA
```

Primers:

```
(SEQ ID N°10) AACCTAAGGCCACCTCCAAT (right)
(SEQ ID N°11) GCAAACCTAAGGCCACCTC (right)
(SEQ ID N°12) ATTCACCCCATGCCCTAAG (left)
```

The following conditions were used to amplify markers M1 and M2 simultaneously:

| The following conditions were used to amplify markers M1 and M2 simultaneously: | |
|---|---|
| 10 × buffer, Promega | 1.5 µl |
| $MgCl_2$ Promega | 1.5 µl |
| dNTP (5 mM) | 0.6 µl |
| M1-1 primer (10 mM) | 0.15 µl |
| M1-4 primer (10 mM) | 0.15 µl |
| M2-1 primer (10 mM) | 0.15 µl |
| M2-2 primer (10 mM) | 0.15 µl |
| $H_2O$ | 7.74 µl |
| Taq Polymerase | 0.06 µl |
| DNA (5 ng/µl) | 3.00 µl |
| PCR programme: | |
| 5 min at 94° C. | |

-continued 1 mn at 94° C.
30 s at 59° C.
1 mn at 72° C.
35 cycles
5 mn at 72° C.
10 mn at 4° C.

PCR programme:

5 min at 94° C.
1 mn at 94° C.
30 s at 59° C.
1 mn at 72° C.
35 cycles
5 mn at 72° C.
10 mn at 4° C.

The M2 marker may be amplified alone at a hybridization temperature of 60.5° C., the other parameters remaining unchanged. Under these amplification conditions, the M2 marker appears to be a dominant marker characterized by band presence in the sensitive parent (IR64) and band absence in the Gigante parent.

Example 11

Creation of a Population of Recombinant Resistant Plants Between Markers M1 and M2 to Arrange within this Space the Candidate AFLP Markers for Resistance Marking 750 F2 individuals (IR64×Gigante) were artificially inoculated with the RYMV virus (BF1 strain). The symptom-free plants were transplanted to a greenhouse, i.e. 188 individuals. Subsequently, additional analysis based on ELISA and descendant tests made it possible to eliminate a last fraction of 50 sensitive plants. The remaining 138 plants, homozygote for resistance, were systematically genotyped for both markers M1 and M2 as previously described. In this manner, 45 individuals were selected (38 recombinant relative to M1. 7 recombinant relative to M2) and 2 double recombinants. These recombinant individuals were used for arranging the AFLP markers in the space between M1 and M2. These results are summarized in Table 6 below:

TABLE 6

Selection of a recombinant F2 sub-population (IR64 × Gigante) in the M1–M2 marker space

| Steps conducted: F2 (IR64 × Gigante) | N° of plants | % |
|---|---|---|
| Inoculation of F2 plants (10 days after sowing) | 768 | |
| Greenhouse transplantation (5 weeks after inoculation) | 188 | |
| Elimination of sensitive plants (symptom follow-up - Elisa test, descendant test) | 50 | |
| Selection of homozygote resistant plants for the bred resistance gene | 138 | 17.9 |
| Genotyping of selected individuals for markers M1 and M2 | | |
| Recombinant plants relative to M1 | 36 | 18.8 |
| Recombinant plants relative to M1 and M2 | 2 | 1.4 |
| Recombinant plants relative to M2 | 7 | 5.1 |

Example 12

Screening of AFLP Markers to Select New Candidate Markers for Resistance

A total of 328 primer pairs EcoRI/MseI, each one defined by 3 nucleotides, was used following the protocol previously described. These primers are given in Table 7 below.

TABLE 7

| Combination N° | EcoRI primer | MesI primer |
|---|---|---|
| 1 | AAC | CAA |
| 2 | AAC | CAC |
| 3* | AAC | CAG |
| 4 | AAC | CAT |
| 5 | AAC | CCA |
| 6 | AAC | CCT |
| 7 | AAC | CGA |
| 8 | AAC | CGT |
| 9 | AAC | CTA |
| 10 | AAC | CTC |
| 11 | AAC | CTG |
| 12 | AAC | CTT |
| 13 | AAC | AAC |
| 14 | AAC | AAG |
| 15 | AAC | AAT |
| 16 | AAC | ACA |
| 17 | AAC | ACC |
| 18 | AAC | ACG |
| 19 | AAC | ACT |
| 20 | AAC | AGC |
| 21 | AAC | AGG |
| 22 | AAC | AGT |
| 23 | AAG | CAA |
| 24 | AAG | CAC |
| 25 | AAG | CAG |
| 26 | AAG | CAT |
| 27 | AAG | CCA |
| 28 | AAG | CCT |
| 29 | AAG | CGA |

TABLE 7-continued

| | | |
|---|---|---|
| 30 | AAG | CGT |
| 31 | AAG | CTA |
| 32 | AAG | CTC |
| 33 | AAG | CTG |
| 34 | AAG | CTT |
| 35 | AAG | AAC |
| 36 | AAG | AAG |
| 37 | AAG | AAT |
| 38 | AAG | ACA |
| 39 | AAG | ACC |

| | | |
|---|---|---|
| 40 | AAG | ACG |
| 41 | AAG | ACT |
| 42 | AAG | AGC |
| 43 | AAG | AGG |
| 44 | AAG | AGT |
| 45 | ACA | CAA |
| 46 | ACA | CAC |
| 47 | ACA | CAG |

| | | |
|---|---|---|
| 48 | ACA | CAT |
| 49 | ACA | CCA |
| 50 | ACA | CCT |
| 51 | ACA | CGA |
| 52 | ACA | CGT |
| 53 | ACA | CTA |
| 54 | ACA | CTC |

| | | |
|---|---|---|
| 55 | ACA | CTG |
| 56 | ACA | CTT |
| 57 | ACA | AAC |
| 58 | ACA | AAG |
| 59 | ACA | AAT |
| 60 | ACA | ACA |
| 61 | ACA | ACC |
| 62 | ACA | ACG |
| 63 | ACA | ACT |
| 64 | ACA | AGC |
| 65 | ACA | AGG |

TABLE 7-continued

| | | |
|---|---|---|
| 66 | ACA | AGT |
| 67 | ACC | CAA |
| 68 | ACC | CAC |
| 69** | ACC | CAG |
| 70 | ACC | CAT |
| 71 | ACC | CCA |
| 72 | ACC | CCT |
| 73 | ACC | CGA |
| 74 | ACC | CGT |

| | | |
|---|---|---|
| 75 | ACC | CTA |
| 76 | ACC | CTC |
| 77** | ACC | CTG |
| 78 | ACC | CTT |
| 79 | ACC | AAC |
| 80 | ACC | AAG |
| 81** | ACC | AAT |
| 82 | ACC | ACA |
| 83 | ACC | ACC |

| | | |
|---|---|---|
| 84 | ACC | ACG |
| 85 | ACC | ACT |
| 86** | ACC | AGC |
| 87 | ACC | AGG |
| 88 | ACC | AGT |
| 89 | ACG | CAA |
| 90 | ACG | CAC |
| 91** | ACG | CAG |
| 92 | ACG | CAT |
| 93 | ACG | CCA |

| | | |
|---|---|---|
| 94 | ACG | CCT |
| 95 | ACG | CGA |
| 96 | ACG | CGT |
| 97 | ACG | CTA |
| 98 | ACG | CTC |
| 99 | ACG | CTG |
| 100 | ACG | CTT |
| 101 | ACG | AAC |

TABLE 7-continued

| 102 | ACG | AAG |
| --- | --- | --- |
| 103 | ACG | AAT |
| 104* | ACG | ACA |
| 105 | ACG | ACC |
| 106 | ACG | ACG |
| 107 | ACG | ACT |
| 108 | ACG | AGC |

| 109 | ACG | AGG |
| --- | --- | --- |
| 110 | ACG | AGT |
| 111 | ACT | CAA |
| 112 | ACT | CAC |
| 113 | ACT | CAG |
| 114 | ACT | CAT |
| 115 | ACT | CCA |
| 116 | ACT | CGT |
| 117 | ACT | CGA |
| 118 | ACT | CGT |
| 119 | ACT | CTA |

| 120 | ACT | CTC |
| --- | --- | --- |
| 121 | ACT | CTG |
| 122 | ACT | CTT |
| 123 | ACT | AAC |
| 124 | ACT | AAG |
| 125 | ACT | AAT |
| 126 | ACT | ACA |
| 127 | ACT | ACC |
| 128 | ACT | ACG |

| 129 | ACT | ACT |
| --- | --- | --- |
| 130 | ACT | AGC |
| 131 | ACT | AGG |
| 132 | ACT | AGT |
| 133 | AGA | CAA |
| 134 | AGA | CAC |
| 135 | AGA | CAG |
| 136 | AGA | CAT |
| 137 | AGA | CCA |

| 138 | AGA | CCT |
| --- | --- | --- |
| 139 | AGA | CGA |
| 140 | AGA | CGT |
| 141 | AGA | CTA |
| 142 | AGA | CTC |
| 143 | AGA | CTG |
| 144 | AGA | CTT |
| 145 | AGA | AAC |
| 146 | AGA | AAG |
| 147 | AGA | AAT |

| 148 | AGA | ACA |
| --- | --- | --- |
| 149 | AGA | ACC |
| 150 | AGA | ACG |
| 151 | AGA | ACT |
| 152 | AGA | AGC |
| 153 | AGA | AGG |
| 154*** | AGA | AGT |
| 155 | AGC | CAA |

| 156 | AGC | CAC |
| --- | --- | --- |
| 157*** | AGC | CAG |
| 158 | AGC | CAT |
| 159 | AGC | CCA |
| 160 | AGC | CCT |
| 161 | AGC | CGA |
| 162 | AGC | CGT |

| 163 | AGC | CTA |
| --- | --- | --- |
| 164 | AGC | CTC |
| 165 | AGC | CTG |
| 166 | AGC | CTT |
| 167 | AGC | AAC |
| 168 | AGC | AAG |
| 169 | AGC | AAT |
| 170 | AGC | ACA |
| 171 | AGC | ACC |
| 172 | AGC | ACG |
| 173 | AGC | ACT |

TABLE 7-continued

| | | |
|---|---|---|
| 174** | AGC | AGC |
| 175*** | AGC | AGG |
| 176 | AGC | AGT |
| 177 | AGC | CAA |
| 178 | AAC | CAC |
| 179 | AGG | CAG |
| 180 | AGG | CAT |
| 181 | AGG | CCA |
| 182 | AGG | CCT |
| 183 | AGG | CGA |
| 184 | AGG | CGT |
| 185 | AGG | CTA |
| 186 | AGG | CTC |
| 187 | AGG | CTG |
| 188 | AGG | CTT |
| 189 | AGG | AAC |
| 190 | AGG | AAG |
| 191 | AGG | AAT |
| 192 | AGG | ACA |
| 193 | AGG | ACC |
| 194 | AGG | ACG |
| 195** | AGG | ACT |
| 196 | AGG | AGC |
| 197*** | AGG | AGG |
| 198 | AGG | AGT |
| 199 | AGT | CAA |
| 200 | AGT | CAC |
| 201 | AGT | CAG |
| 202 | AGT | CAT |
| 203 | AGT | CCA |
| 204 | AGT | CCT |
| 205 | AGT | CGA |
| 206 | AGT | CGT |
| 207 | AGT | CTA |
| 208 | AGT | CTC |
| 209 | AGT | CTG |
| 210 | AGT | CTT |
| 211 | AGT | AAC |
| 212 | AGT | AAG |
| 213* | AGT | AAT |
| 214 | AGT | ACA |
| 215** | AGT | ACC |
| 216 | AGT | ACG |
| 217 | AGT | ACT |
| 218 | AGT | AGC |
| 219 | AGT | AGG |
| 220* | AGT | AGT |
| 221 | ATC | CAA |
| 222 | ATC | CAC |
| 223 | ATC | CAG |
| 224 | ATC | CAT |
| 225 | ATC | CCA |
| 226 | ATC | CCT |
| 227 | ATC | CGA |
| 228 | ATC | CGT |
| 229 | ATC | CTA |
| 230 | ATC | CTC |
| 231 | ATC | CTG |
| 232 | ATC | CTT |
| 233*** | ATC | AAC |
| 234*** | ATC | AAG |
| 235* | ATC | AAT |
| 236 | ATC | ACA |
| 237 | ATC | ACC |
| 238 | ATC | ACG |
| 239 | ATC | ACT |
| 240 | ATC | AGC |
| 241 | ATC | AGG |
| 242 | ATC | AGT |
| 243 | CAA | CAA |
| 244 | CAA | CAC |
| 245 | CAA | CAG |
| 246 | CAA | CAT |
| 247 | CAA | CCA |
| 248 | CAA | CCT |
| 249 | CAA | CGA |
| 250** | CAA | CGT |
| 251 | CAA | CTA |
| 252 | CAA | CTC |
| 253 | CAA | CTG |

TABLE 7-continued

| | | |
|---|---|---|
| 254* | CAA | CTT |
| 255 | CAA | AAC |
| 256 | CAA | AAG |
| 257* | CAA | AAT |
| 258** | CAA | ACA |
| 259 | CAA | ACC |
| 260 | CAA | ACG |
| 261 | CAA | ACT |
| 262 | CAA | AGC |
| 263 | CAA | AGG |
| 264 | CAA | AGT |
| 265 | CAT | CAA |
| 266 | CAT | CAC |
| 267 | CAT | CAG |
| 268 | CAT | CAT |
| 269 | CAT | CCA |
| 270 | CAT | CCT |
| 271 | CAT | CGA |
| 272* | CAT | CGT |
| 273 | CAT | CTA |
| 274 | CAT | CTC |
| 275 | CAT | CTG |
| 276 | CAT | CTT |
| 277 | CAT | AAC |
| 278 | CAT | AAG |
| 279 | CAT | AAT |
| 280* | CAT | ACA |
| 281 | CAT | ACC |
| 282 | CAT | ACG |
| 283 | CAT | ACT |
| 284 | CAT | AGC |
| 285 | CAT | AGG |
| 286 | CAT | AGT |
| 287* | ACT | CAA |
| 288 | CTA | CAC |
| 289 | CTA | CAG |
| 290 | CTA | CAT |
| 291* | CTA | CCA |
| 292 | CTA | CCT |
| 293 | CTA | CGA |
| 294 | CTA | CGT |
| 295 | CTA | CTA |
| 296 | CTA | CTC |
| 297* | CTA | CTG |
| 298 | CTA | CTT |
| 299 | CTA | AAC |
| 300 | CTA | AAG |
| 301 | CTA | AAT |
| 302 | CTA | ACA |
| 303 | CTA | ACC |
| 304 | CTA | ACG |
| 305 | CTA | ACT |
| 306 | CTA | AGC |
| 307 | CTA | AGG |
| 308 | CTA | AGT |
| 309 | CTT | CAA |
| 310 | CTT | CAC |
| 311 | CTT | CAG |
| 312** | CTT | CAT |
| 313 | CTT | CCA |
| 314 | CTT | CCT |
| 315 | CTT | CGA |
| 316 | CTT | CGT |
| 317 | CTT | CTA |
| 318* | CTT | CTC |
| 319** | CTT | CTG |
| 320 | CTT | CTT |
| 321 | CTT | AAC |
| 322 | CTT | AAG |
| 323 | CTT | AAT |
| 324 | CTT | ACA |
| 325 | CTT | ACC |
| 326 | CTT | ACG |
| 327 | CTT | ACT |
| 328 | CTT | AGT |

Shaded: polymorphism for one or more bands between the sensitive and resistant pools
*presence of one or more polymorphous bands in sensitive pool
**presence of one or more polymorphous bands in resistant pool
***presence of one or more polymorphous bands in sensitive pool and resistant pool With this screening, it was possible to identify one or more polymorphous bands according to their occurrence in the sensitive parent and/or resistant parent. 23 primer pairs were able to identify polymorphism between the parents confirmed by the F2 DNA pools, sensitive or resistant. The table below summarizes and gives the position in the M1–M2 space of the AFLP markers bound to the locus of bred resistance to the rice yellow mottle virus.

TABLE 8

| Combination Number | Variable nucleotides | | Presence of band(s) | | Marker position in M1–M2 space |
| --- | --- | --- | --- | --- | --- |
| | EcoRI primer | MseI primer | Sensitive pool | Resistant pool | |
| 3 | AAC | CAG | + | − | = cloned M1 marker |
| 69 | ACC | CAG | + | − | = cloned M2 marker |
| 77 | ACC | CTG | − | + | non-determined |
| 81 | ACC | AAT | − | + | non-determined |
| 86 | ACC | AGC | − | + | non-determined |
| 91 | ACG | CAG | − | + | non-determined |
| 104 | ACG | ACA | + | − | betw. R and Rm273 |
| 154 | AGA | AGT | + | + | beyond M2 |
| 157 | AGC | CAG | − | + | in cosegr with M2 |
| 174 | AGC | AGC | − | + | non-determined |
| 175 | AGC | AGG | + | + | betw M1 and Rm241 |
| 197 | AGG | AGG | + | + | betw M1 and Rm241 |
| 215 | AGT | ACC | − | + | non-determined |
| 220 | AGT | AGT | + | − | betw Rm273 and M2 |
| 233 | ATC | AAG | + | + | betw M1 and Rm241 |
| 250 | CAA | CGT | − | + | non-determined |
| 254 | CAA | CTT | + | − | beyond M2 |
| 258 | CAA | ACA | + | − | betw M1 and Rm241 |
| 280 | CAT | ACA | + | − | beyond M2 |
| 287 | CTA | CAA | + | − | betw Rm273 and M2 |
| 291 | CTA | CCA | + | − | betw M1 and Rm241 |
| 318 | CTT | CTC | + | + | bewt Rm273 and M2 |
| 319 | CTT | CTG | − | + | non-determined |

After separate verification on each of the individuals forming the pools, the candidate markers corresponding to bands present in the IR64 parent may be tested on the recombinants identified in example 11. In this manner, 9 markers were confirmed as belonging to the M1–M2 space. Table 9 gives the order in the M1–M2 space of the AFLP markers identified by comparing sensitive and resistant DNA pools from a resistant F2 sub-population (IR64×Gigante).

TABLE 9

| F2 Resistant individuals (IR64 x Gigante) | M1 | E-AGG M-AGG | E-ATC M-AGG | E-CAA M-ACA | E-AGC M-AGG | E-CTA M-CCA | RM241 | RM252 | RYMV resist | E-ACG M-ACA | RM273 | E-AGT M-AGT | C-CTT M-CTC | E-CTA M-CAA | M2 |
|---|---|---|---|---|---|---|---|---|---|---|---|---|---|---|---|
| 2 | H | D | D | D | D | D | – | B | B | B | B | B | B | B | B |
| 7 | H | D | D | D | D | D | – | B | B | B | B | B | B | B | B |
| 8 | H | D | D | D | D | D | – | B | B | B | B | B | B | B | B |
| 10 | H | D | D | D | E | D | – | B | B | B | B | B | B | B | B |
| 21 | H | D | D | D | D | B | C | B | B | B | B | B | B | B | B |
| 23 | H | D | D | D | E | D | – | B | B | B | B | B | B | B | B |
| 25 | H | D | D | D | D | D | E | H | B | B | B | B | B | B | |
| 28 | H | D | D | D | B | B | C | B | B | B | B | B | B | B | B |
| 37 | H | D | D | D | E | D | E | H | B | B | B | B | B | B | B |
| 48 | H | D | D | D | D | D | – | B | B | B | B | B | B | B | B |
| 55 | H | D | D | D | D | D | E | H | B | B | B | B | B | B | B |
| 61 | H | D | D | D | D | D | E | H | B | B | B | B | B | B | B |
| 65 | H | D | D | D | – | B | C | B | B | B | B | B | B | B | B |
| 95 | H | E | D | D | D | B | C | B | B | B | B | B | B | B | B |
| 103 | H | E | D | D | – | B | C | B | B | B | B | B | B | B | B |
| 104 | H | D | D | D | B | B | C | B | B | B | B | B | B | B | B |
| 109 | H | B | B | B | B | B | C | B | B | B | B | B | B | B | B |
| 111 | H | E | D | D | D | D | – | B | B | B | B | B | B | B | B |
| 119 | H | D | D | D | D | D | – | B | B | B | B | B | B | B | B |
| 120 | A | D | D | D | D | B | C | B | B | B | B | B | B | B | B |
| 125 | H | E | E | E | E | D | – | B | B | B | B | B | B | B | B |
| 127 | H | – | – | – | – | B | C | B | B | B | B | B | B | B | B |
| 131 | H | E | E | E | E | D | – | B | B | B | B | B | B | B | B |
| 133 | H | – | – | – | – | B | C | B | B | B | B | B | B | B | B |
| 141 | H | E | E | E | E | D | E | H | H | B | B | B | B | B | B |
| 154 | H | E | E | E | E | D | – | B | B | B | B | B | B | B | B |
| 158 | H | E | E | E | E | D | – | B | B | B | B | B | B | B | B |

TABLE 9-continued

| | | | | | | | | | | | | | | | |
|---|---|---|---|---|---|---|---|---|---|---|---|---|---|---|---|
| 159 | H | – | – | – | – | B | C | B | B | B | B | B | B | B | B |
| 160 | H | E | E | E | E | D | – | B | B | B | B | B | B | B | B |
| 151 | H | E | E | E | E | D | – | B | B | B | B | B | B | B | B |
| 153 | H | – | – | – | – | B | C | B | B | B | B | B | B | B | B |
| 157 | H | – | – | – | – | B | B | B | B | B | B | B | B | B | B |
| 171 | H | – | – | – | – | B | B | B | B | B | B | B | B | B | B |
| 175 | H | E | E | E | D | D | B | B | B | B | B | B | B | B | B |
| 179 | H | – | – | – | B | B | B | B | B | B | B | B | B | B | B |
| 183 | H | E | E | E | E | D | B | B | B | B | B | B | B | B | B |
| 35 | H | D | D | D | D | D | H | H | B | D | H | D | D | D | D |
| 135 | H | E | E | E | E | D | H | H | B | B | H | D | D | D | D |
| 17 | H | B | B | B | B | – | B | B | D | H | D | D | D | D |
| 20 | B | B | B | B | B | B | B | B | D | H | D | D | D | D |
| 38 | B | B | B | B | B | B | – | B | B | D | H | D | D | D | D |
| 93 | B | B | B | B | B | B | B | B | D | H | D | D | D | D |
| 105 | B | B | B | B | B | B | B | B | B | D | H | D | D | D | D |
| 145 | B | – | – | – | B | B | B | B | B | B | B | B | B | B | D |
| 180 | B | – | – | B | B | B | B | B | B | B | D | D | D | D |

Incidence of recombinant individuals*
M1-R space 0.97 0.97 0.97 0.87 0.61 0.29 0.13
R-M2 space 0.67 0.78 0.89 0.89 0.89
Distance/resistance (cM) 11.4 11.03 11.03 11.03 9.88 6.90 3.33 2.10 0.00 3.33 3.89 4.44 4.44 4.44 5.0
A: genotype homozygote for the allele of the sensitive parent (IR64)
H: heterozygote genotype
B: homozygote genotype for the allele of the resistant parent (Gigante)
D: genotype non homozygote for the allele of the resistant parent (Gigante)
*under the assumption of absence of double combination in space M1-R and M2-R
**estimated distance using resistance map on 183 F2 (IR64 × Gigante) cf (FIG. X)
14 bands from the resistant parent were also identified and will or will not be confirmed on recombinants generated in the F2 population (IR64 × Gigante).

Example 13

Anchoring of the RYMV Resistance Locus Using Microsatellite Markers

Figure 10:
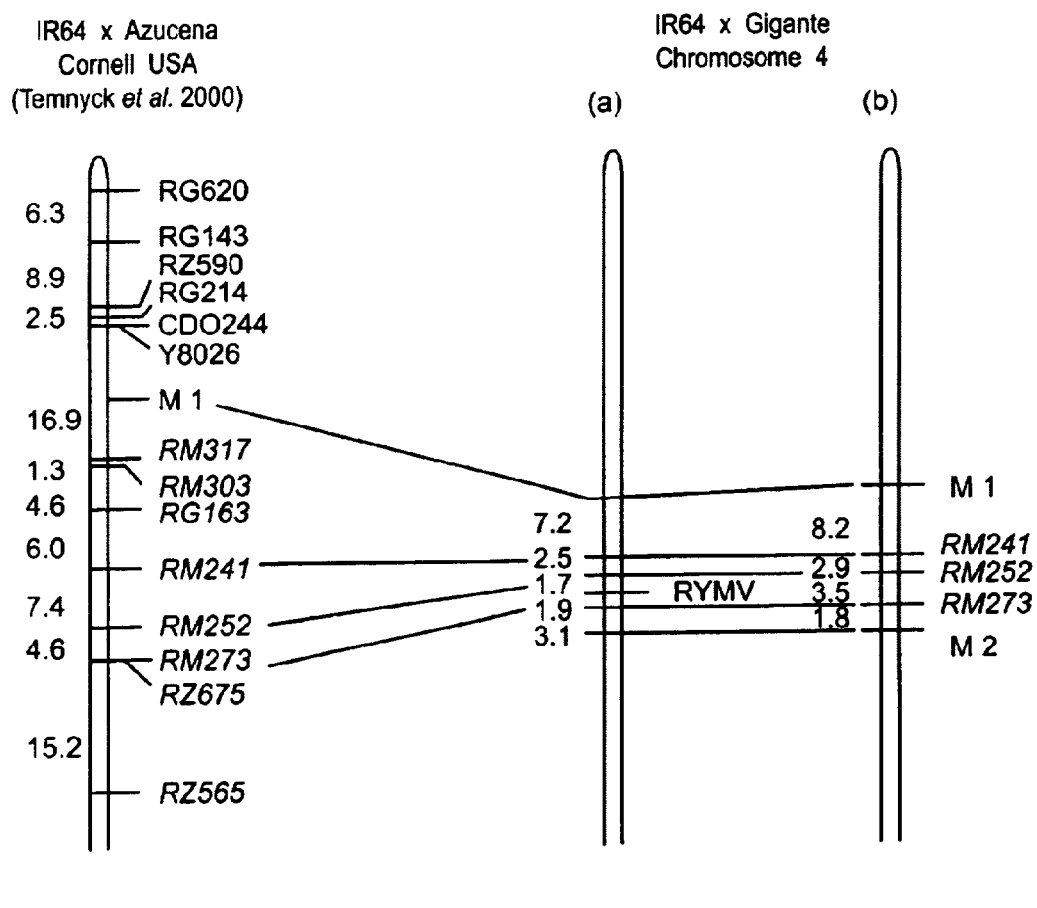
FIG. 10: mapping and anchoring of the locus of bred resistance to RYMV on the map IR64×Azucena.
Figure 11:
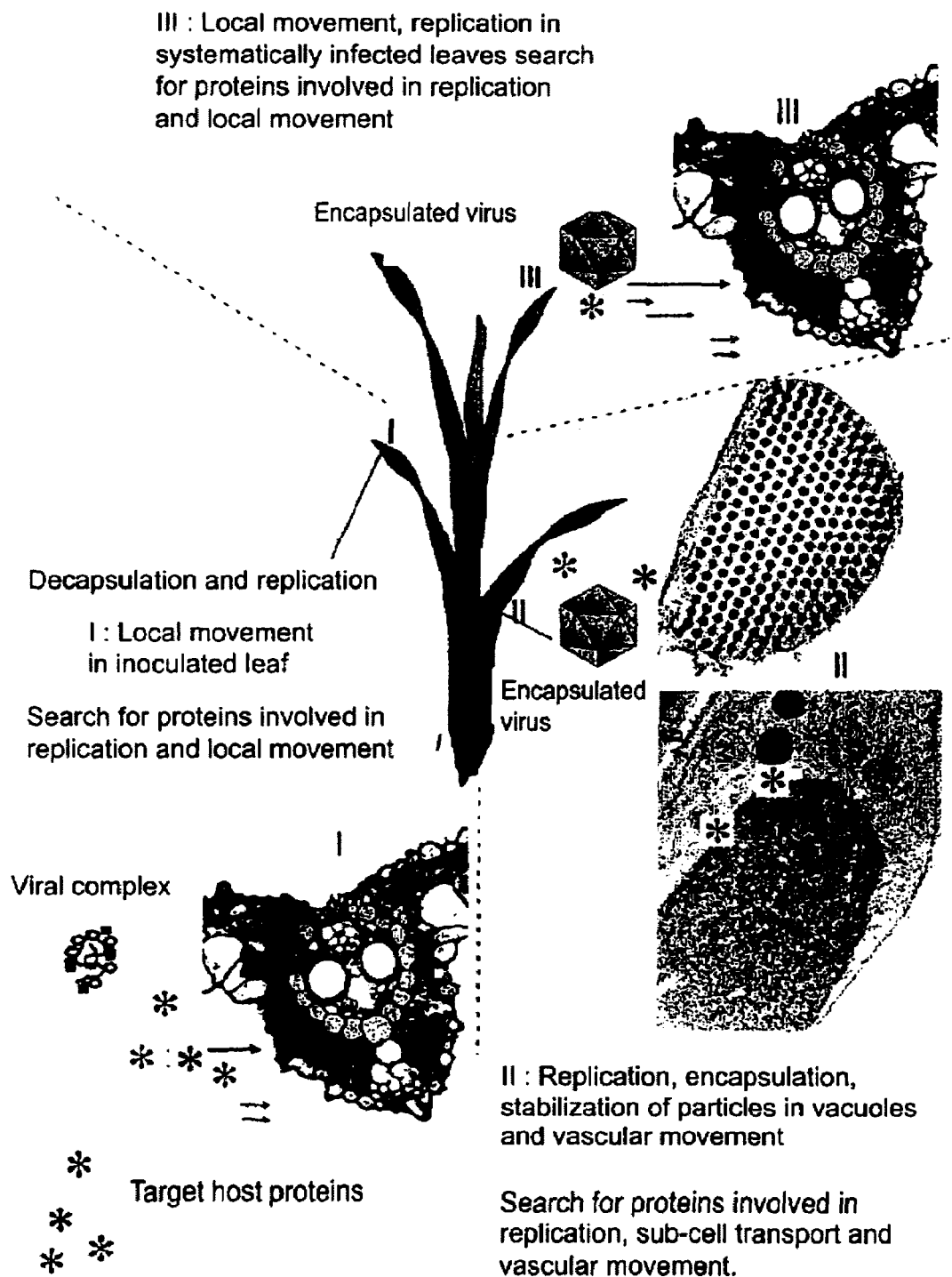
FIG. 11: movement of the RYMV virus in a plant, after inoculation in a leaf.

The M1 marker being positioned on chromosome 4 of the genetic map (IR64×Azucena; example 9) microsatellite markers such as defined in (6) and belonging to this chromosome were used to fine-tune the map of the RYMV resistance locus. The following microsatellite markers were tested: RM241, RM252 (1), RM273 and RM177(6), under the experimental conditions described in (1) and (6). With the exception of the RM177 marker, non-polymorphous between the IR64 and Gigante parents, the markers RM241, RM252, RM273 were mapped on a F2 population (IR64× Gigante) assessed in parallel for RYMV resistance. The results on 183 F2 individuals make it possible to characterized a stretch of approximately 3.6 cM bordered by the two microsatellite loci RM252 and RM272 surrounding the RYMV resistance gene (see FIG. 10(*a*)).

Example 14

Fine Mapping of the Space Carrying the Resistance Locus and Order of the Resistance Markers in the M1–M2 Space The 45 F2 individuals (IR64×Gigante) resistant and recombinant for the M1 and m2 markers were characterized for the microsatellite markers identified in example 13. The mapping of the markers in segregation on all the F2 individuals (IR64×Gigante) available (321) confirms the order and the distance between the markers of the M1–M2 space, in particular the RM252–RM273 space which is estimated at 3.6 cM (FIG. 10(*b*)). With the 45 F2 individuals (IR64× Gigante) that are resistant and recombinant for the M1 and M2 markers, it is possible to confirm the order of the AFLP markers identified in example 12. One AFLP marker, EACG/MACA, remains within the RM252–RM273 space and represents the nearest marker to the RYMV resistance locus (Table 9). Overall, out of the 321 F2 individuals tested, there are 20 individuals recombined on one side or other of the RYMV resistance locus and may advantageously be used to identify closer markers and/or for cloning the resistance gene.

Example 15

Marker-Assisted Resistance Transfer

The markers close to the resistance locus were tested on irrigated varieties highly sensitive to the RYMV virus (var BG90-2, Bouaké189, Jaya). 3 markers (M1, RM241, RM252) show polymorphism between these 3 varieties and the Gigante variety, enabling the use of these markers to be considered for resistance transfer to sensitive genotypes. Experimental transfer of resistance to these varieties was made as far as the $2^{nd}$ backcross. At each cross, the plants were verified for the presence of markers derived from Gigante, and resistance segregation was controlled by descendant tests on F2. Table 10 below summarizes results.

TABLE 10

| Recurrent parent | Polymorphism/donor parent (Gigante) | | | | | Generation obtained | theoretical % recurrent parent | N° of lines obtained |
|---|---|---|---|---|---|---|---|---|
| | M1 | RM241 | RM252 | RM273 | RM177 | | | |
| BG90-2 | poly | poly | poly | — | — | BC2F2 | 87.5 | 4 |
| Bouaké | poly | poly | poly | — | — | BC2F2 | 87.5 | 1 |
| 189 | poly | poly | poly | — | — | BC2F2 | 87.5 | 2 |
| Jaya IR64 | poly | poly | poly | poly | mono | BC3 | 93.7 | 5 |

Example 16

Use of the RYMV Virus or the Virus/Ribonucleoproteins Complex as Bait to Capture the Target Proteins Essential to the RYMV Infectious Cycle I—In Vitro and In Vivo Characterization of Three Independent Calcium and pH Isoforms of RYMV.

Three isoforms are described using ion exchange chromatography, the principle of this separation being based on the stability of the particles.

The compact forms are the most stable since they are blocked by the divalent calcium ions making the particle insensitive to pH. This form does not attach to the ion exchange resin and passes through the column unharmed. The transitional forms are described for the first time and result from compact particles or swollen particles. These particles are calcium-free, which makes them sensitive to pH. Therefore, at acid pH, they are maintained compact, whereas at basic pH they are swollen. These two isoforms (compact and transitional) can be differentiated by changing the pH in the chromatography buffer. At basic pH, the transitional particles swell instantaneously and explode in the column as they are insufficiently stable to tolerate chromatography pressure (approximately 1000 to 1500 psi); The capsid protein resulting from this dissociation attaches to the ion exchange resin. The compact forms are therefore purified at a basic pH. The swollen forms are very difficult to isolate on account of their instability, but may be produced from compact particles in the presence of a divalent ion chelater (EDTA or EGTA) and at basic pH. After this treatment, all the particles become unstable and explode inside the column.

According to the invention, to capture the target proteins, the following are used:

i) The compact particle obtained after dialysis in 10 mM sodium acetate pH 5.0 and 3 mM $CaCl_2$, approximately 6 hours and purification by chromatography at pH 8.0. Target proteins isolated after extraction of the virus from infected plants or after exposure of compact particles (purified by Biocad) and proteins extracted from cell suspension of a variety sensitive to the virus (IR64).

ii) The transitional particle is obtained from the compact particle in the presence of EDTA and at acid pH.

iii) The swollen particle and the ribonucleic complex are obtained from transitional particles at basic pH. At this pH, the ribonucleoprotein complex is spontaneously obtained from swollen particles (highly unstable).

II Method for Capturing Target Proteins:

From the Virus Extracted from Infected Sensitive Plants (IR64)

The results are shown in FIG. 12. FIG. 12A: control chromatograph with no injection at pH 8.5; FIG. 12B: chromatograph after injection of 100 μl virus at 1.7 μg/μl, pH 8.5, method 1 (NaCl gradient of 0 to 2550 mM); FIG. 12C: chromatograph after injection of 100 μl virus dialysed for approximately 14 h in 10 mM sodium acetate, pH 5 and 3 mM $CaCl_2$; FIG. 12D: chromatograph after injection of 100 μl virus (non dialysed) at 1.7 μg/μl, pH 8.5, method 2 (NaCl gradient of 0 to 1500 mM and 1500 to 2550 mM, see method after examples). Collection of fractions (1 ml), acetone precipitation 800 μl, 2 hours at 4° C., centrifuging 20 minutes 13000 r.p.m., residue speed-vac dried 5 min, then replaced in suspension in approximately 40 μl 10 mM Tris-base buffer, pH 7.4. The samples are stored in the freezer at −20° C.

Figure 13A:
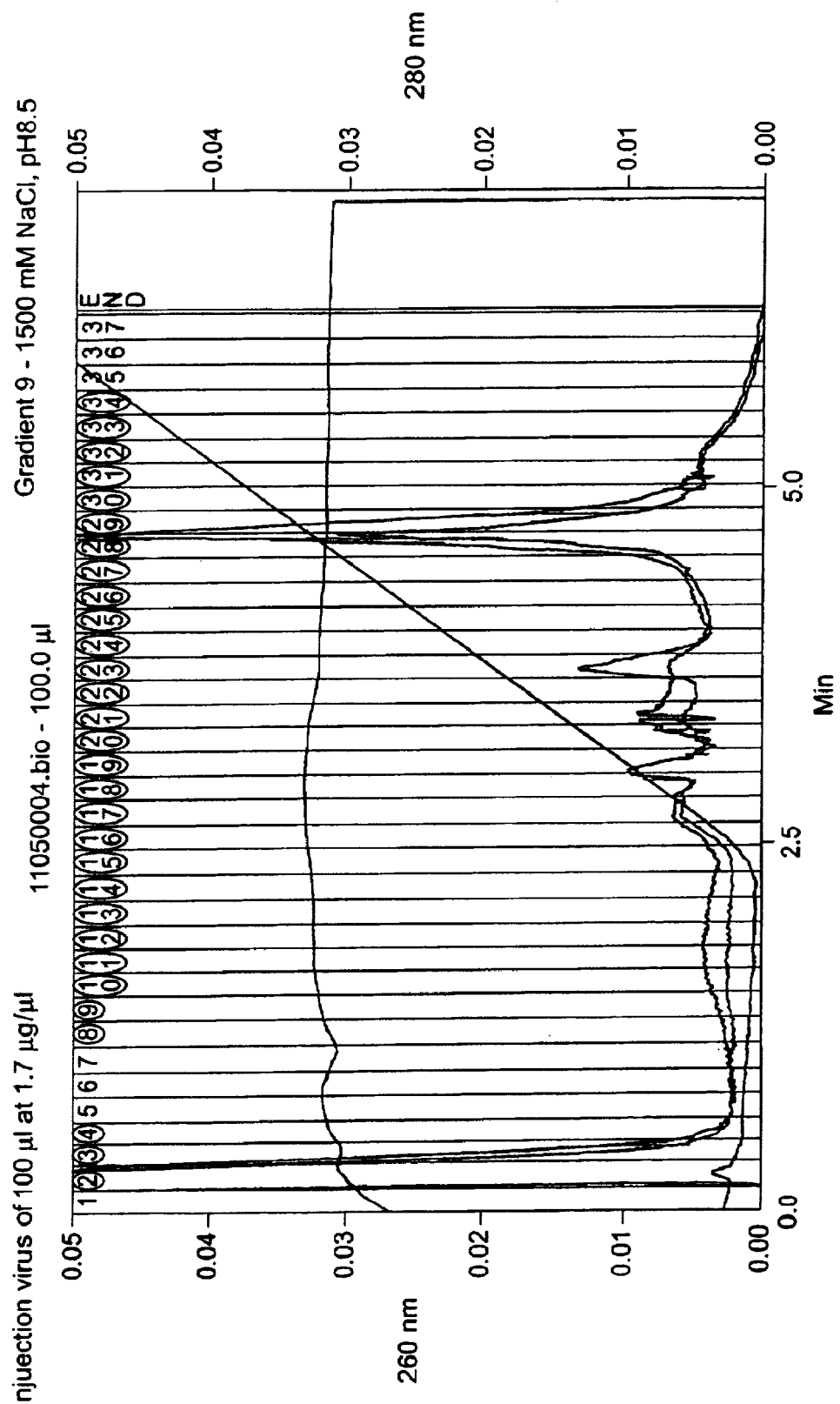
FIG. 13: a chromatograph after virus injection, a SDS PAGE gel and an immunoblot with a capsid anti-protein antibody.
Figure 13B:
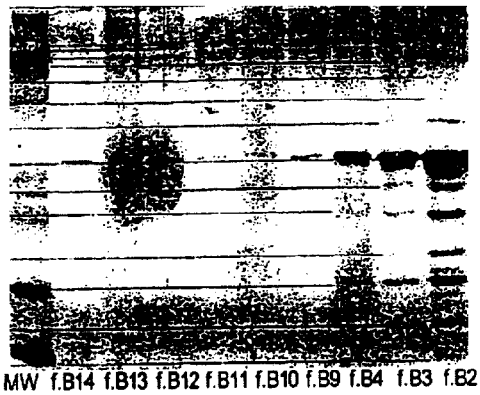
Figure 13C:
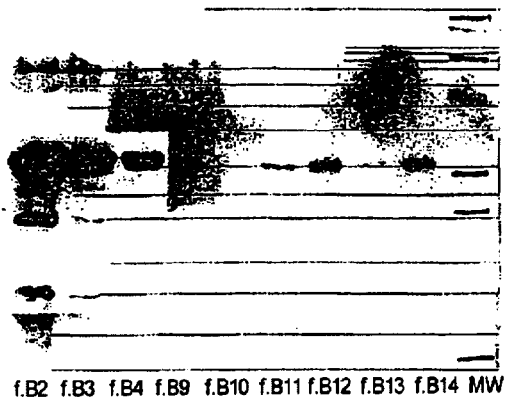
Figure 13C:
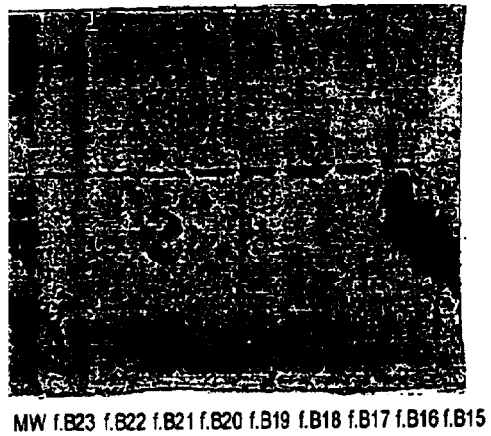
Figure 13C:
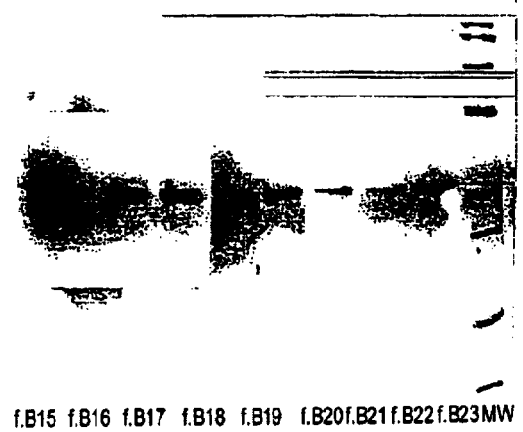

After injection of 170 μg virus in the Biocad at pH 8.0, method 1 (FIG. 13A), the different fractions are collected, acetone precipitated, recovered in a 10 mM Tris-base buffer, pH 7.4 and deposited on SDS-PAGE mini-gel, and the gel is subsequently developed with silver nitrate (Biorad) (FIG. 13B) and Western-Blot (FIG. 13C) using a capsid anti-protein MabE.5 non-discriminating monoclonal antibody (Denis Fargette, IRD).

The non-immunodetected bands correspond to plant proteins of potential interest. These are proteins of 5, 24, 42, 49, 59, 66, 70, 77 and 210 kDa.

From Extracted, Dialysed Virus (for Approximately 14 h in 10 mM sodium acetate pH 5.0 and 3 mM $CaCl_2$) Subsequently Purified on Biocad=Fraction 2 (A2).

The virus is contacted with the proteins of the rice cell suspension (IR 64) to trap the target proteins.

Figure 14A:
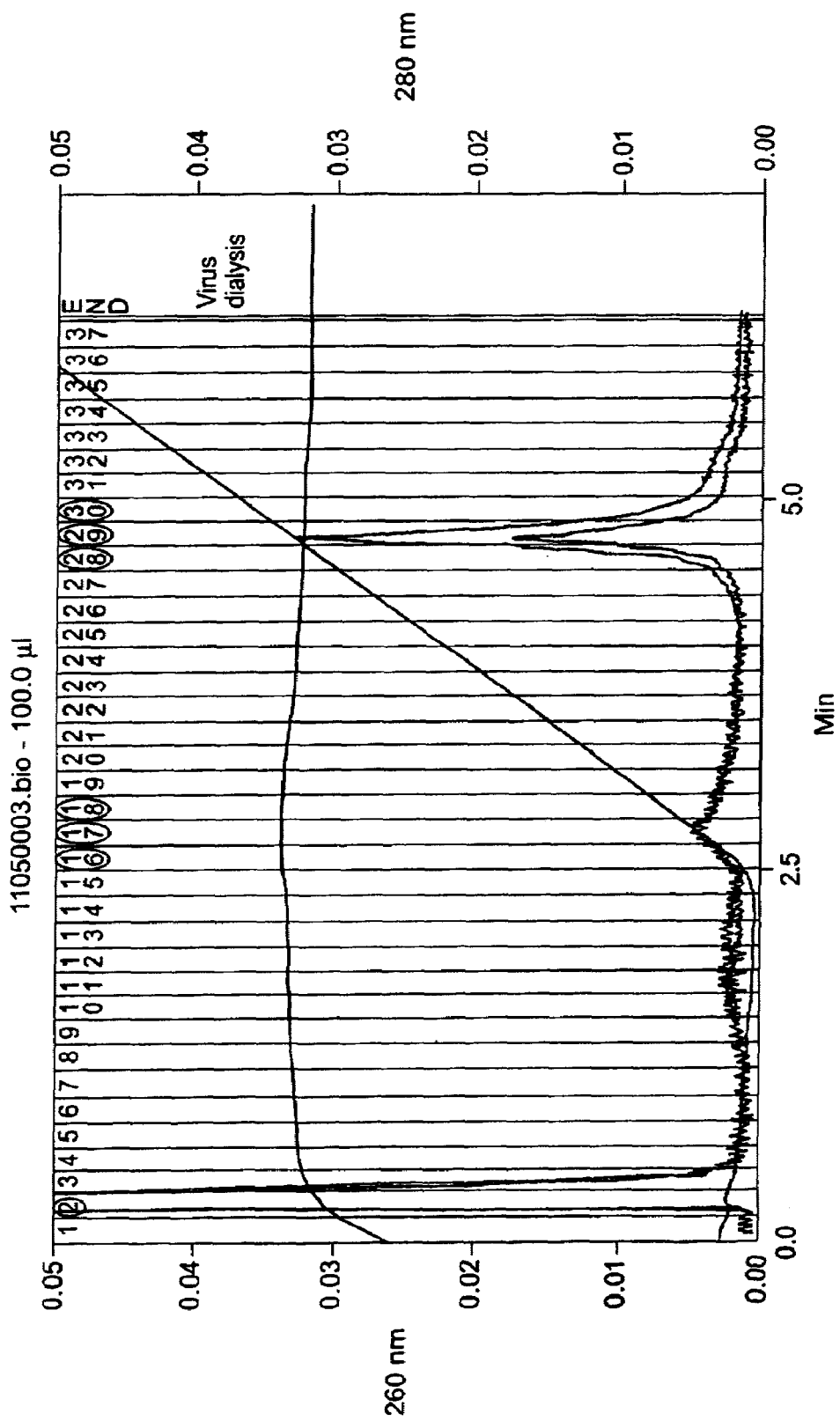
FIG. 14: a chromatograph and a SDS PAGE gel.
Figure 14B:
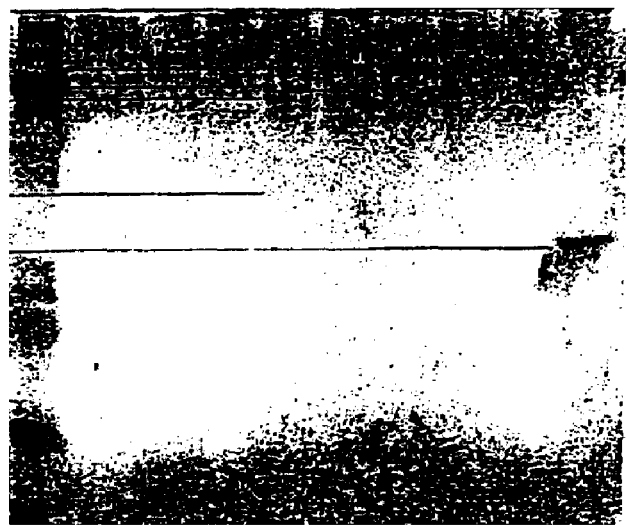
Figure 14C:
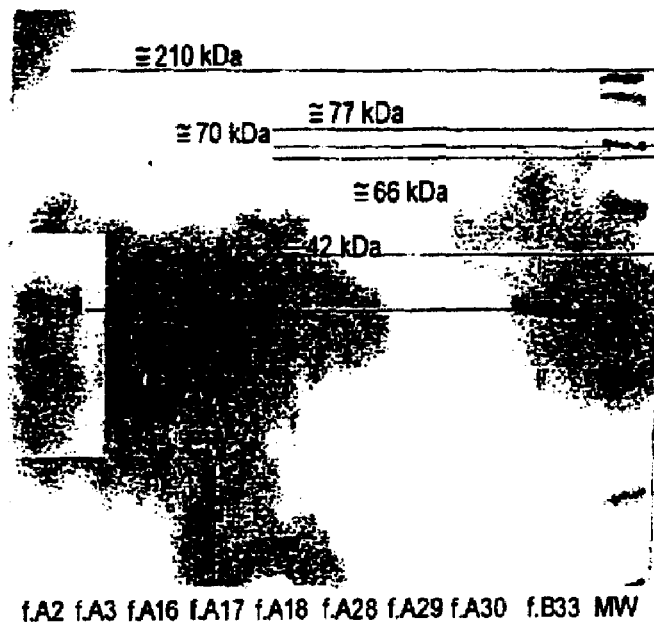
Figure 15A:
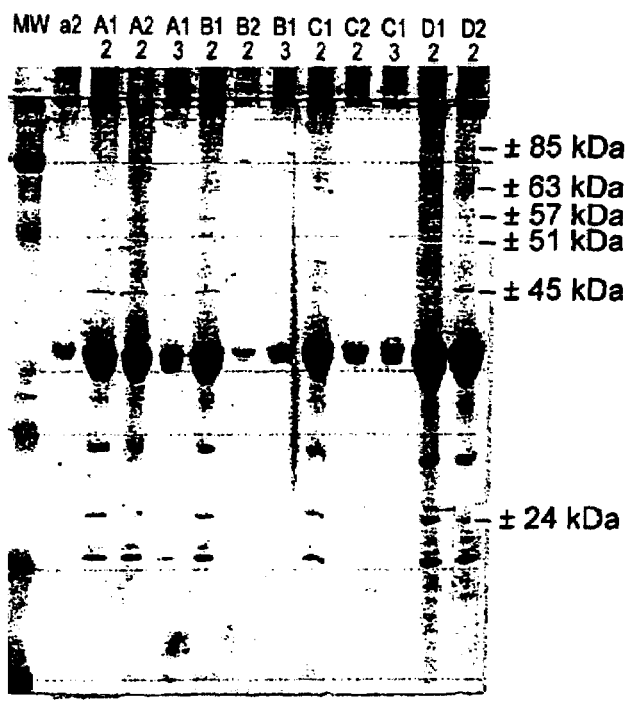
FIG. 15: a SDS PAGE gel and an immunoblot with a capsid anti-protein antibody.
Figure 15B:
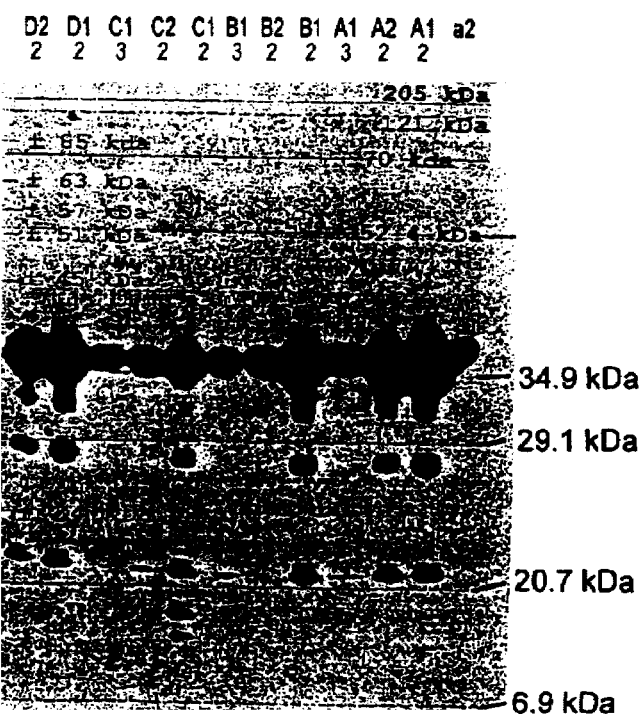

Purification and verification of the purity of fraction 2 (FIG. 14A). In fraction 2, the virus is pure since there is no longer any presence of sub-bands detected after SDS-PAGE gel and silver nitrate development (FIGS. 14B and 14C, fraction A2 to be compared with B2 in FIGS. 13B and 13C). After incubation of 350 µg of the virus and 860 µg of proteins extracted from a cell suspension (IR64) at 4° C. for 12 hours in different incubation solutions (FIG. 15), the samples are extracted with or without NaCl. The samples are then purified on Biocad, and the viral fraction after acetone precipitation (fraction 2 and 3) is analysed on large SDS-PAGE gel stained with silver nitrate (FIG. 15A) and immunodetection with Mab E.5 (FIG. 15B).

The target proteins (non-immunodetected by Mab E.5) have similar molecular weights to those isolated from the infected leaves; they are particularly visible under D2 conditions (pH8.0 with 10 mM DTT and 0.3M NaCl); they are the proteins 24, 45, 51, 57, 63, 85 and proteins located beyond 120 kDa.

III—Cloning of Target Proteins and Use for the Identification of a New Class of Resistance Genes.

The isolated target proteins are sequenced at their N-terminal end (proteins 24, 42–45 kDa, proteins in the region of 57, 63 and 85 kDa and proteins beyond 120 kDa). The degenerate 5' primers are identified. Cloning of cDNA is carried out in the banks of the varieties indica (IR64 and Gigante), temperate japonica (02428), tropical japonica (Azucena) and glaberrima (TOG 5681 and TOG 5673). The sequences are then analysed using conventional techniques (homology, putative function and polymorphism).

IV—Materials and Methods

Extraction of the virus: Extraction is performed by means of steps consisting of: harvesting fresh leaves (or stored at –80° C.) from plants infected by the virus (the symptoms must be marked). The period of infection depends upon the variety of rice used (the tolerant varieties can be used to obtain a greater quantity of virus).

Grind the leaves in liquid nitrogen to obtain a fine powder, and cold store.

Add the extraction buffer (0.1M sodium acetate*, pH: 5.0) to which is added 0.2% β-mercaptoethanol (≈1 liter buffer for 100 g crushed leaves) and shake for 2 mn.

Filter the suspension obtained with "cheesecloth" type fabric and hand press the residue remaining in the cloth Add 1 part chloroform and shake for 2 mn.

Centrifuge at 10000 g for 10 mn at 4° C. and collect the upper aqueous phase;

Evaluate the volume of the aqueous phase and add NaCl to obtain a final concentration of 0.3M. Leave to dissolve (in cold chamber) and add PEG8000 for a final concentration of 6%.

Leave under shaking overnight (precipitation of the viruses)

Centrifuge the suspension for 30 mn at 22000 g at 4° C. in 250 ml jars

Discard the supernatant and air-dry the virus residue for a few minutes. Collect the residue of each jar in 1 ml of extraction buffer (1) and replace in cold suspension.

Group together the fractions obtained and rinse the jars with 0.5 ml buffer which is added to the previous fractions.

Centrifuge 10 mn at 12000 g to remove solid impurities and collect the supernatant.

After dilution, conduct spectrophotometer assay at 259 nm and calculate the concentration of the virus:

in which 6.5 corresponds to O.D. 259 of a 1 μg/μl viral suspension.

A ratio of $$\frac{O.D.259}{O.D.280} \geq 1.5$$

evidences good purification of the virus, otherwise perform a purification on sucrose gradient.

*Solution A: 2M acetic acid (115.5 in 1000 ml) and solution B: 2M sodium acetate (164 g $C_2H_3O_2$ or 272 g $C_2H_3O_2Na$, $3H_2O$ in 1000 ml.

14.8 ml of solution A+35.2 ml of solution B in 1000 ml overall, first add solution B then solution A gradually until pH 5 is reached; adjust pH if necessary with solution A.

Ion Exchange Chromatography

Biosystems PerSeptive Chromatograph BIOCAD 700E (Framingham, Mass., USA) with a Gilson F-250 fraction collector. Samples of 100 μl of virus are injected and purified on a prepacked POROS anionic ion exchange column (HQ//H, 4.6 mm D/100 mm L, CV=1.7 ml), a column containing particles of 10 μm POROS. The elution buffer used is made up of 15 mM Bis-Tris Propane: Tris base (50/50 Sigma) at pH 6 or pH 8.5 at a flow rate of 6 ml/mn for an inner pressure of around 1500 psi. Before injection, the column is equilibrated with the elution buffer. After injection of the virus, the column is washed with the elution buffer, then with NaCl gradient of 0 to 2.55 M for 3 min (method 1) or with a NaCl gradient of 0 to 1550M for 4 minutes, then with a gradient of 1500 mM to 2550 mM for 30 seconds (method 2). Finally, a last step (approximately 1 minute) with the elution buffer and a NaCl concentration of 2550 mM is conducted. Absorbency is recorded at 260 and 280 nm. After 3 injections of the same sample, the maximum variation observed is approximately 3%. The minimum detection level for the virus is approximately 7 ng/μl. The 1 ml fractions are collected and dialysed for approximately 14 h at 4° C. in the 20 mM phosphate buffer before injection. The samples are examined under electronic microscope.

Cell Suspension

The grains are shelled, then placed in 70 (v/v) ethanol to disinfect for 1 minute, and then in a solution of 2.6% sodium hypochlorite setting up a partial vacuum for improved contact for 45 mn.

After 4 washings in sterile water, the grains are placed in the gelled medium (MS medium) in Petri dishes (sealed with parafilm) and placed in the dark at 25° C.

Six weeks later, the calli developed from the embryo are placed in culture in a liquid medium used for cell multiplication (several globular formations from several calli, using Erlen).

Three weeks later, the calli placed in culture in liquid medium have propagated and the suspensions are transplanted. The suspensions are subsequently transplanted every 10–15 days and the proteins extracted.

Culture Media for Rice Cell Suspensions

SZ Medium (Zhand et al 1998)

MACRO ELEMENTS×10 (per 1 liter)

100 ml mother solution per liter of end solution

| KNO₃ | 40.00 g |
| (NH₄)₂SO₄ | 3.30 g |
| MgSO₄, 7H₂O | 2.46 g |
| NaH₂PO4 | 2.76 g (2H₂O: 3.12 g - anhydrous: 2.40 g) |
| CaCl₂, 2H₂O | 1.47 g |

B5 MACRO ELEMENTS×100 (per 1 liter)

10 ml mother solution per liter of end solution

| MnSO₄, 7H₂O | 1349 mg |
| ZnSO₄ | 112 mg (7H₂O: 200 mg) |
| KI | 75 mg |
| Na₂MoO₄, 2H₂O | 25 mg |
| H₃BO₃ | 300 mg |
| CuSO₄, 5H₂O | 2.5 mg |
| CoCl₂, 6H₂O | 2.5 mg |

B5 VITAMINS×100 (per 100 milliliters)

1 ml mother solution per liter of end solution

| Nicotinic acid | 100 mg |
| Thiamine-HCl | 1000 mg |
| Pyridoxine-HCl | 100 ml |
| Myo-Inositol | 10 g |
| Proline | 500 mg/end litre |
| Glutamine | 500 mg/end litre |
| Enzymatic casein hydrolysate | 300 mg/end litre |

Iron EDTA×1000 (per 1 liter)

A ml mother solution per liter of end solution

| Otherwise | FeSO₄, 7H₂O | 2.8 g |
| | Na₂EDTA | 3.7 g |

HORMONE 2,4-D×1000

1 ml mother solution per liter of end solution

Stock solution at 2 mg/ml

MALTOSE AND SUCROSE (FOR 2428) at 30 g/l pH 5.8

Induction Media for Rice Callogenesis

M.S. (Murashige T. & Skoog F. 1962)

MACRO ELEMENTS×10 (per 1 liter)

100 ml mother solution per liter of end solution

| KNO₃ | 19.00 g |
| NH₄NO₃ | 16.50 g |
| MgSO₄, 7H₂O | 3.70 g |
| KH₂PO4 | 1.70 g |
| CaCl₂, 2H₂O | 4.40 g |

MICRO ELEMENTS×100 per 1 liter)

10 ml mother solution per liter of end solution

| MnSO₄, H₂O | 1690 mg |
| ZnSO₄, 7H₂O | 860 mg |
| KI | 83 mg |
| Na₂MoO₄, 2H₂O | 25 mg |
| H₃BO₃ | 620 mg |
| CuSO₄, 5H₂O | 2.5 mg |
| CoCl₂, 6H₂O | 2.5 mg |

VITAMINS×1000 (per 100 milliliters)

1 ml mother solution per liter of end solution

| Nicotinic acid | 50 mg |
| Thiamine-HCl | 10 mg |
| Pyridoxine-HCl | 50 mg |
| Myo-Inositol | 10 g |
| Glycine | 200 mg |

Iron EDTA×1000 (per 1 liter)

1 ml mother solution per liter of end solution

| Otherwise | FeSO₄, 7H₂O | 2.8 g |
| | Na₂EDTA | 3.7 g |

HORMONE 2.4-D×1000

1 ml mother solution per liter of end solution

Stock solution at 2 mg/ml

MALTOSE OR SUCROSE at 30 g/l pH 5.8

PHYTAGEL 2.5 g/liter

NB (Calli induction and subculture medium)

N6 MACRO ELEMENTS×10 (per 1 liter)

100 ml mother solution per liter of end solution

| KNO₃ | 28.30 g |
| (NH₄)₂SO₄ | 4.64 g |
| MgSO₄, 7H₂O | 1.40 g |
| KH₂PO4 | 4.00 g |
| CaCl₂, H₂O | 1.65 g |

B5 MICRO ELEMENTS×100 (per 1 liter)

10 ml mother solution per liter of end solution

| MnSO₄, 7H₂O | 1349 mg |
| ZnSO₄ | 112 mg (7H2O:200 mg) |
| KI | 75 mg |
| Na₂MoO₄, 2H₂O | 25 mg |
| H₃BO₃ | 300 mg |

-continued

|           |          |        |
|-----------|----------|--------|
| CuSO₄, 5H₂O |        | 2.5 mg |
| CoCl₂, 6H₂O |        | 2.5 mg |

B5 VITAMINS×1000 (per 100 milliliters)

1 ml mother solution per liter of end solution

|                            |         |
|----------------------------|---------|
| Nicotinic acid             | 100 mg  |
| Thiamine-HCl               | 1000 mg |
| Pyridoxine-HCl             | 100 mg  |
| Myo-Inositol               | 10 g    |

Or Gamborg vitamins at 11.2

Add: final concentration

|                              |                   |
|------------------------------|-------------------|
| Proline                      | 500 mg/end litre  |
| Glutamine                    | 500 mg/end litre  |
| Enzymatic casein hydrolysate | 300 mg/end litre  |

Iron EDTA×1000 (per 1 liter)

1 ml mother solution per liter of end solution

|           |                |         |
|-----------|----------------|---------|
| Otherwise | FeSO₄, 7H₂O    | 2.8 mg  |
|           | Na₂EDTA        | 3.7 g   |

Or Ferric sodium salt EDTA (Sigma E-6760) at 4.15 g/l

HORMONE 2,4-D×1000

1 ml mother solution per liter of end solution

Stock solution at 2 mg/ml

MALTOSE AND SUCROSE at 30 g/l

PHYTAGEL 2.6 g/liter pH5.8

Protein Extraction

Extraction of Proteins from Cell Suspensions

Extraction buffer for cell suspensions:

|                             | final concentration | per 100 ml           |
|-----------------------------|---------------------|----------------------|
| Tris                        | 20 mM, pH 7.4       | 50 ml 40 mM Tris pH 7.4 |
| NaCl                        | 100 mM              | 584 mg               |
| Na₂EDTA, 2H₂O               | 10 mM               | 372 mg               |
| Glucose                     | 25 mN               | 856 mg               |
| SDS (denaturing)            | 0.1%                | 0.5 ml 20% SDS       |
| Triton-x-100 (non-denaturing) | 0.1%              | 100 µl               |
| DNAs and RNAs Protein inhibitors | 1 µg/ml        | 2 pellets or 4 ml conc. sol. |
| EGTA                        | 5 mM                | 190 mg               |

|          | final concentration | per 100 ml |
|----------|---------------------|------------|
| Glycerol | 5%                  | 5 ml       |
| DTT      | 5 mM                | 77 mg      |

Readjust pH to 7.4 with HCl 5 g cell suspension are placed in a mortar with sterilised Fontainebleau sand Add 1 ml buffer and grinding, then add 4 ml buffer The rice varieties are hence extracted under denaturing conditions (buffer with SDS) and under non-denaturing conditions (buffer with Triton). Centrifuging 15 mn, 15000 g at 3° C.

Collection and aliquots of 1 ml supernatant in 1.5 ml tubes which are immediately stored at −80° C. All the steps are made as far as possible on ice, and as quickly as possible.

Protein Assay

A reference range of 1000 µg/ml at 100 µg/ml is made with BSA (2 mg/ml) for each denaturing and non-denaturing buffer.

The 4 samples are diluted 5 times in the respective buffers

At 50 µl of each sample and range point, 2.5 ml of Coomassie® Protein Assay reagent are added and then mixed Spectro reading at 595 in disposable tanks

Operating Mode for Membrane Preparation

The acrylamide gels (19:1 or 29:1) are prepared in the following manner:

|                                | Per 1 mm gel |
|--------------------------------|--------------|
| 12% running gel            |              |
| 40% acrylamide bis-acrylamide  | 1.5 ml       |
| 1.5M Tris-HCl pH 8.8           | 1.3 ml       |
| 20% SDS                        | 25 µl        |
| 10% ammonium persulfate        | 50 µl        |
| Temed                          | 5 µl         |
| H₂O                            | 2.2 ml       |
| 5% stacking gel            |              |
| 40% acrylamide bis-acrylamide  | 250 µl       |
| 1M Tris-HCl pH 6.8             | 250 µl       |
| 20% SDS                        | 10 µl        |
| 10% ammonium persulfate        | 20 µl        |
| Temed                          | 2 µl         |
| H₂O                            | 1.5 ml       |

The running gel is poured up to 2 cm from the top of the plate then overlayed with butamol-1 (facilitates polymerisation avoiding air contact)

After polymerisation (15–30 mn), the butanol is removed with Whatmann paper, then the stacking gel is poured and the comb placed in position.

After polymerisation, the wells are washed with migration buffer then the samples previously denatured 5 mn at 98° C. are charged with 1 volume of charge buffer Migration at 80V until blue enters the running gel, then increase to 100V; halt migration when the blue has left the gel (approx. 5 kDa).

Transfer the gels to a 0.45μ nitrocellulose membrane (BIO-RAD ref: 1620115) for 1 h at 100V in the transfer buffer.

Store the moist membranes in the refrigerator until use.

Operating Mode for Use of the Mali Polyclonal Antibody

(Pab Mali)

All the incubation/washing steps are made on a platform shaker of SRP6 Platform Shaker type (Stuart Sciences) at the speed of 20/25 r.p.m. at room temperature≅23° C.

The volumes of solution used for the incubation/washing steps are 20 ml and are made in 112 mm×77 mm plastic boxes.

The membrane is incubated for 1 h with the blocking solution

Incubation 1 h with the $1^{st}$ Polyclonal Mali antibody (anti RYMV) diluted to 1/1000 in the same blocking solution (collect the solution, add the antibody, shake and replace on membrane), 6×5 mn rinsings in TBS pH 7.5

Incubation 1 h with the $2^{nd}$ conjugated HRP-anti-rabbit antibody diluted to 1/40000 in the new blocking solution.

6×5 mn rinsings in TBS pH 7.5

Place the membrane on Saran wrap, and in uniform manner (the membrane must be properly covered) pour the West Pico solution prepared by mixing the 2 solutions in equal volumes (total of 3 ml per small membrane), Wait 5 mn (in the light) remove excess substrate, wrap the membrane in Saran film then place a film on top (in the dark) and expose 1 mn to 1 hour.

For hybridisations at pH 6.5 and pH 8.0 operate in the same manner using MES buffer at pH 6.5 and TAPS buffer at pH 8.0 for all hybridization and washing steps.

Operating Mode for Use of the E Monoclonal Antibody (Mab E)

All the incubation/washing steps are made on a platform shaker of SRP6 Platform Shaker type (Stuart Sciences) at the speed of 20/25 r.p.m. at room temperature≅23° C.

The volumes of solution used for the incubation/washing steps are 20 ml in 112 mm×77 mm plastic boxes.

The membrane is incubated for 1 h with the blocking solution

Incubation 1 h with the $1^{st}$ Monoclonal E antibody (anti-RYMV epitope) diluted to 1/100 or to 1/1000 in the same blocking solution (recover the solution, add the antibody, shake and replace on membrane).

6×5 mn rinsings in TBS pH 7.5.

Incubation 1 h with the $2^{nd}$ conjugated HRP-anti-mouse antibody diluted to 1/40000 in the new blocking solution.

6×5 mn rinsings in TBS pH 7.5

Place the membrane on Saran wrap and in uniform manner (the membrane must be properly covered) pour the West Pico solution prepared by mixing the 2 solutions in equal volumes (total of 3 ml per small membrane).

Wait 5 mn (in the light), remove excess substrate, wrap membrane in Saran, then place film on top (in the dark) and expose for 1 mn to 1 hour.

For the hybridisations at pH6.5 and pH8.0 operate in the same manner using MES buffer at pH 6 and TAPS buffer at pH 8.0 for all hybridisation and washing steps.

Solutions

| Concentration of 2× solution | Quantity product per 10 ml of 2X solution |
|---|---|
| 2× charge buffer: | |
| 100 mM Tris-HCl pH 6.8 | 1 ml 1 M Tris-HCl pH 6.8 |
| 200 mM DTT | 0.308 g |
| 4% SDS | 2 ml 20% SDS |
| 0.2% bromophenol blue | 20 mg |
| 20% glycerol | 2 ml |
| | $H_2O$ to 10 ml final volme |
| 10× Migration buffer | |
| 250 mM Tris base | 30.285 g Tris base |
| 2.5 M glycine | 187.67 g glycine |
| Transfer buffer | |
| Tris base | 2.42 g |
| Glycine | 11.26 g |
| Methanol | 100 ml |
| $H_2O$ | to 1 litre final volume |

Polyclonal blocking solution: 3% non-fat dry milk BIO RAD (ref: 170–6404) in appropriate buffer Monoclonal blocking solution: 0.5% B.S.A. in appropriate buffer TBS pH 7.5: 2.423 f Tris-base (20 mM)+3.146 g NaCl (75 mM)+0.508 g $MgCl_2$, $6H_2O$ (2, mM)+0.5 ml NP-40 (0.05% Tergitol to be heated before use as non-liquid at room temperature)+$H_{20}$ to 1000 ml final volume. Adjust to pH 5.5 with HCl.

MES pH 6.5: 3.904 g MES (20 mM)+4.937 g KCl (75 mM)+0.508 g $MgCl_2$, $6H_2O$ (2.5 mM)+0.5 ml NP-40 (0.05% Tergitol to be heated before use as non-liquid at room temperature)+$H_{20}$ to 1000 ml final volume. Adjust to pH 6.5 with NaOH or HCl.

TAPS pH 8.0: 4.866 g TAPS (20 mM)+4.937 g KCl (75 mM)+0.508 g $MgCl_2$, $6H_2O$ (2.5 mM)+0.5 ml NP-40 (0.05% Tergitol to be heated before use as non-liquid at room temperature)+$H_{20}$ to 1000 ml final volume. Adjust to pH 8.0 with NaOH or HCl.

Polyclonal Mali (Pab Mali): polyclonal antibody solution obtained from the whole viral particle. To be diluted to 1/1000.

Monoclonal E (Mab E): monoclonal antibody solution obtained from a RYMV epitope. To be diluted to 1/50 or 1/1000.

HRP-anti-rabbit conjugated: "ImmunoPure® Goat Anti-Rabbit IgG, (H+ L), Peroxydase Conjugated" (ref PIERCE: 31460) at 0.8 mg/ml after restoring in $H_2O$. Dilute to 1/40000.

HRP-anti-mouse conjugated: "ImmunoPure® Goat Anti-Mouse IgG, (H+ L) Peroxydase Conjugated" (ref PIERCE: 31430) at 0.8 mg/ml after restoring in $H_2O$. Dilute to 1/40000.

West Pico: "SuperSignal® West Pico Chemiluminescent Substrate" (ref PIERCE: 34080). Mix the Lumino/Enhancer Solution and the Stable Peroxydase Solution in equal volumes (total of 3 ml for a small 8 cm×5 cm membrane). The solution so prepared keeps for 24 hours and is used in the light.

REFERENCES (1) Chen, X et al., (1997), Development of a microsatellite framework map providing genome-wide coverage in rice (*Oryza sativa* L) *Theor Appl Genet* 95: 553–567.

(2) Panaud, O. et al., (1996), Development of microsatellite markers and characterization of simple sequence length polymorphism (SSLP) in rice (*Oryza sativa* L) *Mol Gen Genet* 252: 597–607.
(3) Wu K. S. et al., (1993), Abundance, polymorphism and genetic mapping of microsatellites in rice. *Mol Gen Genet* 241: 225–235.
(4) Zabeau et al., (1993), Selective restriction fragment amplification: a general method for DNA fingerprinting. EP 92402629.7.
(5) Vos et al., (1995), AFLP, a new technique for DNA fingerprinting. Nucleic Acids research 23: 4407–4414.
(6) Temnyck et al., (2000), Theor Appl Genet 100:697–712.

What is claimed is:

1. Method for collecting proteins involved in the recognition and targeted transport of a pathogenic virus circulating via the plasmodesmata in a plant, the method comprising subjecting samples containing complexes of said proteins with viral particles to electrophoresis and Western blotting, detecting any material which binds to a capsid anti-protein monoclonal antibody, and collecting non-immunodetected blotting material.

2. The method according to claim 1, wherein the complex is obtained from virus extracted from infected sensitive plants.

3. The method according to claim 2, wherein the virus is the Rice Yellow Mottle Virus (RYMV) and proteins of 5, 24, 42, 49, 59, 66, 70, 77 and 210 kDa are collected.

4. The method according to claim 1, wherein the complex is obtained from purified virus and contacted with the proteins of a cell suspension of a sensitive plant.

5. The method according to claim 4, wherein the virus is the Rice Yellow Mottle Virus (RYMV), and proteins of 24, 45, 51, 57, 63, 85 and beyond 120 kDa are collected.

* * * * *

SEQUENCE LISTING

<160> NUMBER OF SEQ ID NOS: 12

<210> SEQ ID NO 1
<211> LENGTH: 16
<212> TYPE: DNA
<213> ORGANISM: Artificial sequence
<220> FEATURE:
<223> OTHER INFORMATION: Description of artificial sequence: adapter

<400> SEQUENCE: 1
gactgcgtac caattc                                                          16

<210> SEQ ID NO 2
<211> LENGTH: 16
<212> TYPE: DNA
<213> ORGANISM: Artificial sequence
<220> FEATURE:
<223> OTHER INFORMATION: Description of artificial sequence: adapter

<400> SEQUENCE: 2
gatgagtcct gagtaa                                                          16

<210> SEQ ID NO 3
<211> LENGTH: 472
<212> TYPE: DNA
<213> ORGANISM: Artificial sequence
<220> FEATURE:
<223> OTHER INFORMATION: Description of artificial sequence: fragment
      identified as M1 marker

<400> SEQUENCE: 3
cgtgcttgct tatagcacta caggagaagg aaggggaaca caacagccat ggcgagcgaa        60
ggttcaacgt cggagaaaca ggctgcgacg ggcagcaagg tgccggcggc ggatcggagg       120
aaggaaaagg aggaaatcga agttatgctg gaggggcttg acctaagggc agatgaggag       180
gaggatgtgg aattggagga agatctagag gagcttgagg cagatgcaag atggctagcc       240
ctagccacag ttcatacgaa gcgatcgttt agtcaagggg ctttctttgg gagtatgcgc       300
tcagcatgga actgcgcgaa agaagtagat ttcagagcaa tgaaagacaa tctgttctcg       360
atccaattca attgtttggg ggattgggaa cgagttatga atgaaggtcc atggacctttt     420 cgaggatgtt cggtgctcct cgcagaatat gatggctggt ccaagattga at              472

<210> SEQ ID NO 4
<211> LENGTH: 21
<212> TYPE: DNA
<213> ORGANISM: Artificial sequence
<220> FEATURE:
<223> OTHER INFORMATION: Description of artificial sequence: primer

<400> SEQUENCE: 4
aggaagggga acacaacagc c                                                    21

<210> SEQ ID NO 5

-continued

```
<211> LENGTH: 21
<212> TYPE: DNA
<213> ORGANISM: Artificial sequence
<220> FEATURE:
<223> OTHER INFORMATION: Description of artificial sequence: primer

<400> SEQUENCE: 5
ttatgctgga ggggcttgac c                                          21

<210> SEQ ID NO 6
<211> LENGTH: 21
<212> TYPE: DNA
<213> ORGANISM: Artificial sequence
<220> FEATURE:
<223> OTHER INFORMATION: Description of artificial sequence: primer

<400> SEQUENCE: 6
gcagttccat gctgagcgca t                                          21

<210> SEQ ID NO 7
<211> LENGTH: 21
<212> TYPE: DNA
<213> ORGANISM: Artificial sequence
<220> FEATURE:
<223> OTHER INFORMATION: Description of artificial sequence: primer

<400> SEQUENCE: 7
ccgaacatcc tcgaaaggtc c                                          21

<210> SEQ ID NO 8
<211> LENGTH: 21
<212> TYPE: DNA
<213> ORGANISM: Artificial sequence
<220> FEATURE:
<223> OTHER INFORMATION: Description of artificial sequence: primer

<400> SEQUENCE: 8
tcatattctg cgaggagcac c                                          21

<210> SEQ ID NO 9
<211> LENGTH: 121
<212> TYPE: DNA
<213> ORGANISM: Artificial sequence
<220> FEATURE:
<223> OTHER INFORMATION: Description of artificial sequence: fragment
      identified as M2 marker

<400> SEQUENCE: 9
aattcacccc atgccctaag ttaggacgtt ctcagcttag tggtgtggta gcttttctta    60
ttttcctaag cacccattga agtatttttgc attggaggtg gccttaggtt tgcctctgtt  120
a                                                                 121

<210> SEQ ID NO 10
<211> LENGTH: 20
<212> TYPE: DNA
<213> ORGANISM: Artificial sequence
<220> FEATURE:
<223> OTHER INFORMATION: Description of artificial sequence: primer

<400> SEQUENCE: 10
aacctaaggc cacctccaat                                             20

<210> SEQ ID NO 11
<211> LENGTH: 19
<212> TYPE: DNA
```

```
<213> ORGANISM: Artificial sequence
<220> FEATURE:
<223> OTHER INFORMATION: Description of artificial sequence: primer

<400> SEQUENCE: 11
gcaaacctaa ggccacctc                                                    19

<210> SEQ ID NO 12
<211> LENGTH: 19
<212> TYPE: DNA
<213> ORGANISM: Artificial sequence
<220> FEATURE:
<223> OTHER INFORMATION: Description of artificial sequence: primer

<400> SEQUENCE: 12
attcacccca tgccctaag                                                    19
```